(12) United States Patent
Bacus et al.

(10) Patent No.: US 7,862,995 B2
(45) Date of Patent: Jan. 4, 2011

(54) METHODS AND MATERIALS FOR PREDICTING RESPONSIVENESS TO TREATMENT WITH DUAL TYROSINE KINASE INHIBITOR

(75) Inventors: Sarah S. Bacus, Hinsdale, IL (US); Jason Hill, Chicago, IL (US)

(73) Assignee: Targeted Molecular Diagnostics, Westmont, IL (US)

( * ) Notice: Subject to any disclaimer, the term of this patent is extended or adjusted under 35 U.S.C. 154(b) by 0 days.

(21) Appl. No.: 11/223,700

(22) Filed: Sep. 9, 2005

(65) Prior Publication Data

US 2006/0127928 A1    Jun. 15, 2006

Related U.S. Application Data

(60) Provisional application No. 60/635,198, filed on Dec. 10, 2004.

(51) Int. Cl.
| | |
|---|---|
| *C12Q 1/00* | (2006.01) |
| *C12Q 1/68* | (2006.01) |
| *G01N 33/53* | (2006.01) |
| *G01N 33/48* | (2006.01) |
| *A01N 37/18* | (2006.01) |

(52) U.S. Cl. .................... 435/6; 435/4; 435/7.1; 514/2; 702/19

(58) Field of Classification Search ............... None
See application file for complete search history.

(56) References Cited

PUBLICATIONS

Smith et al., Br. J. Cancer, 2004, vol. 91, pp. 1190-1194, Aug. 10, 2004.*
Cobleigh et al., Journal of Clinical Oncology, vol. 17, pp. 2639-2648, 1999.*
Perissi et al., Oncogene, vol. 19, pp. 280-288, 2000.*
Bamberger et al., Hormone Research, vol. 54, pp. 32-37, 2000.*

* cited by examiner

*Primary Examiner*—Shubo (Joe) Zhou
(74) *Attorney, Agent, or Firm*—K&L Gates LLP

(57) ABSTRACT

The present invention relates to a panel of targeted therapy markers that can be used in assessing a particular subject's sensitivity to various therapeutic agents and cancer treatments as a means of prognosticating whether a treatment or use of a particular therapeutic agent will result in a clinically positive outcome. Cellular receptors, ligands to those receptors and molecules involved in the programmed cell death pathway are examples of targeted therapy markers that might be used in the present invention.

11 Claims, 25 Drawing Sheets

FIGURE 1

| Breast Tumors | Non-Breast Tumors |
|---|---|
| • TUNEL<br>• ErbB2<br>• p-ErbB2<br>• IGF-1R<br>• TGF-α<br>• pS6<br>• p-Erk1/2<br>• ER (negative)<br>• PR (negative)<br>• Bcl-2 (negative) | • TUNEL<br>• ErbB2<br>• p-ErbB2<br>• p-Akt<br>• p-Erk1/2<br>• pS6<br>• NDF |

Figure 3
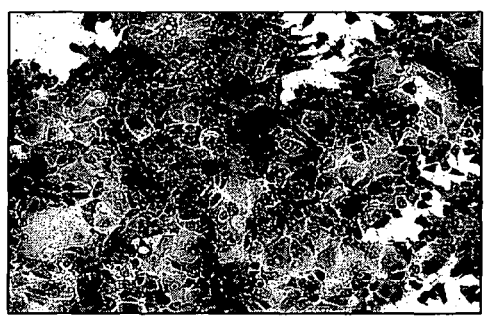
Untreated
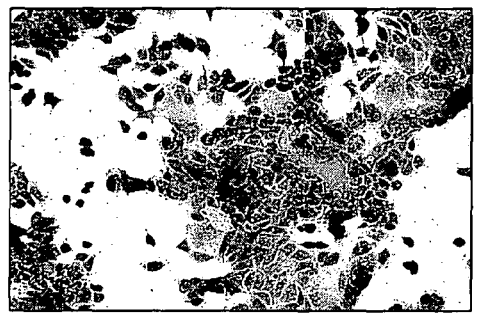
tamoxifen
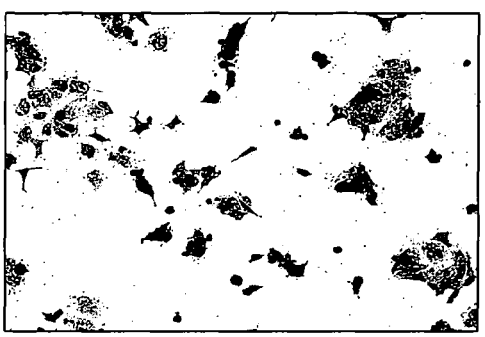
GW2974
GW2974+ tamoxifen

Figure 4
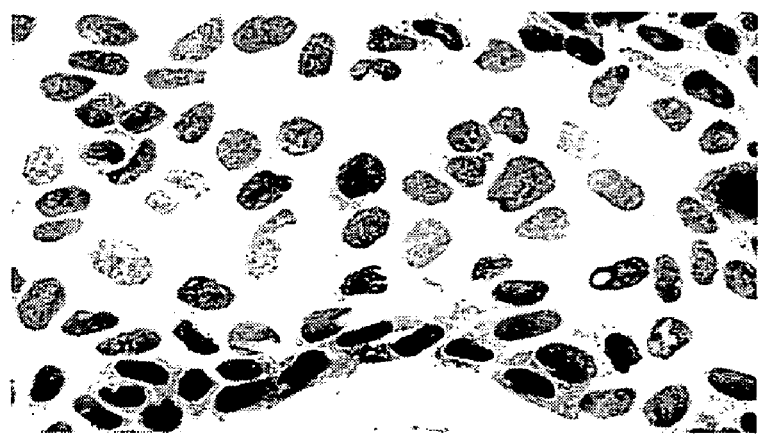
(a) untreated
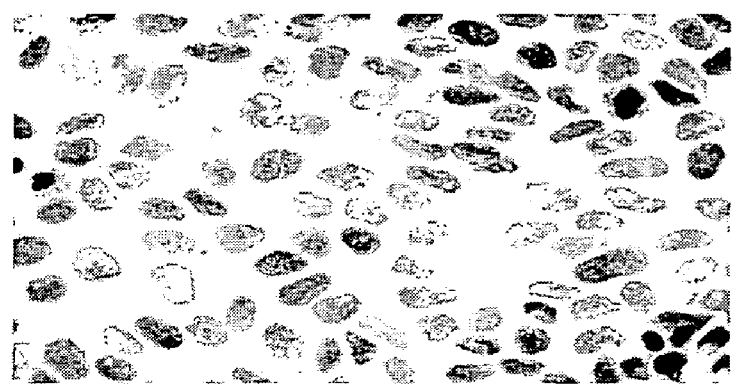
(b) treated by β-estradiol
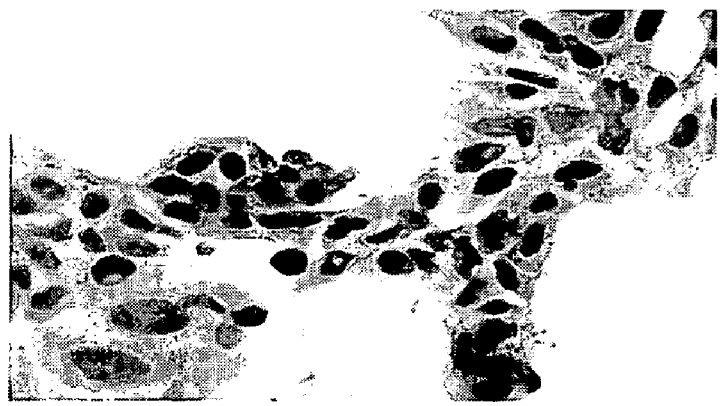
(c) treated by β-estradiol in the presence of GW2974

1 = Untreated

2 = + Estrogen

3 = + GW2974

4 = + Estrogen pre-treatment + GW2974

Figure 11
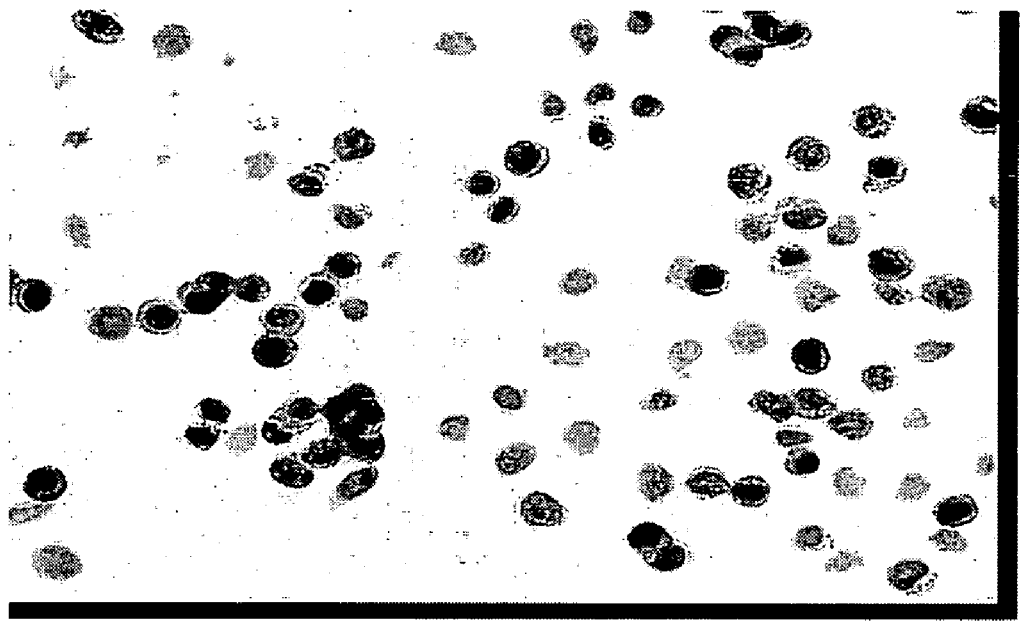
(a) AU-565 Control
(a) AU-565 GW572O16 treated Figure 12
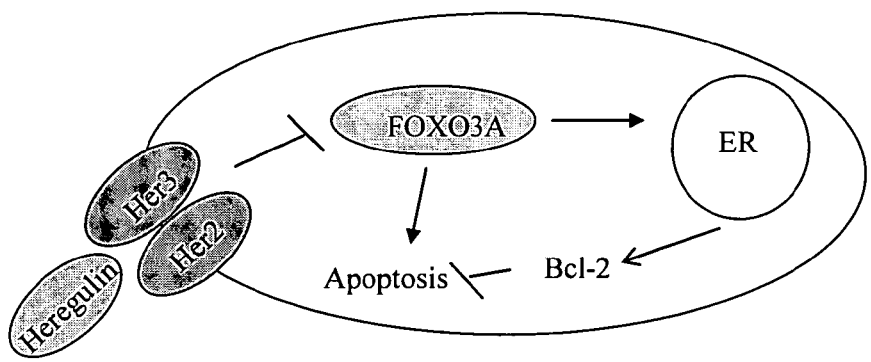
(a) Regulation of FOXO3A, ER, Bcl-2
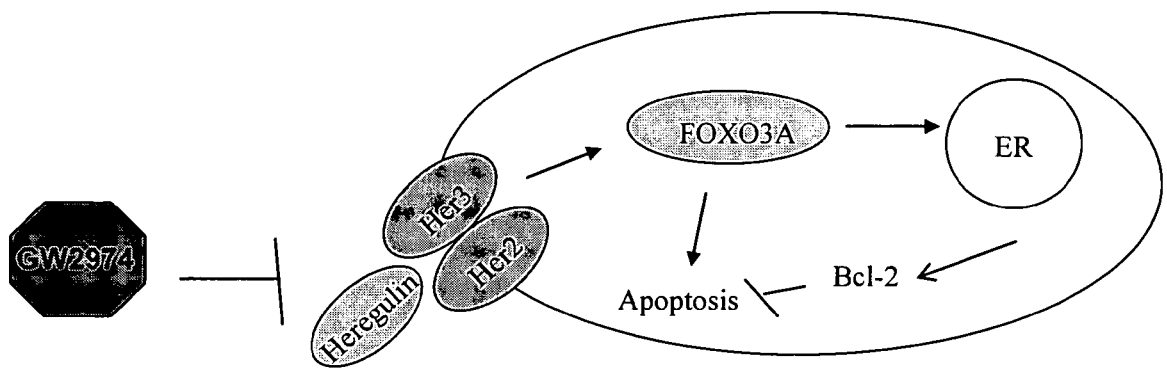
(b) Regulation of FOXO3A, ER, Bcl-2 by GW2974

Figure 14
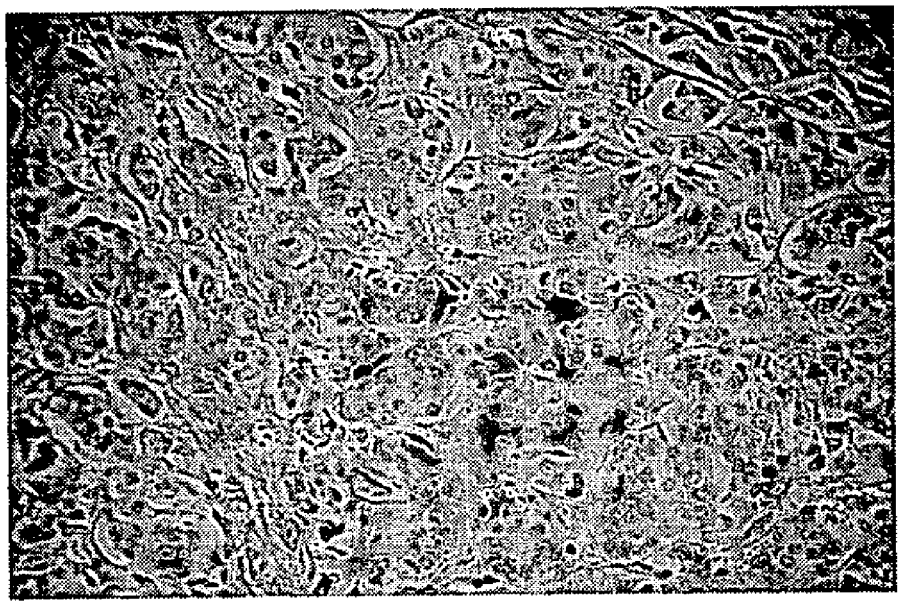
Day 1 Post-Treatment
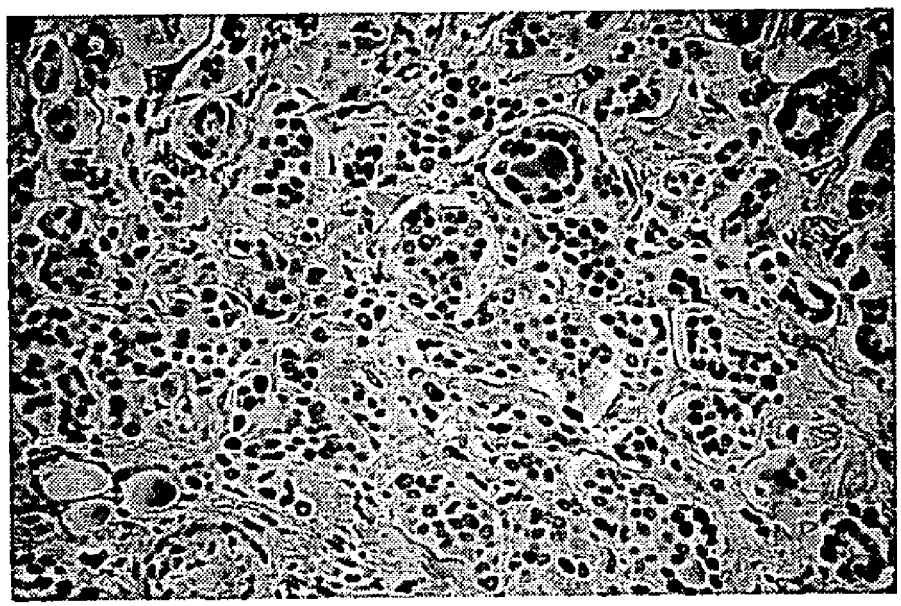
Day 21 Post-Treatment

Figure 16
Biomarker Expression Pre-Treatment
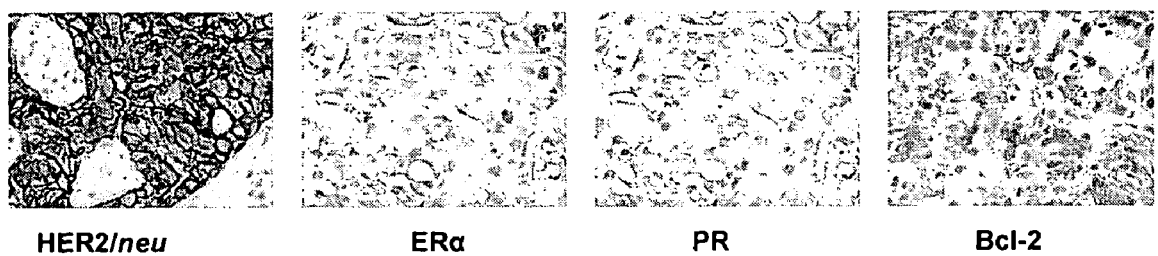
HER2/neu       ERα       PR       Bcl-2
Biomarker Expression Post-Treatment
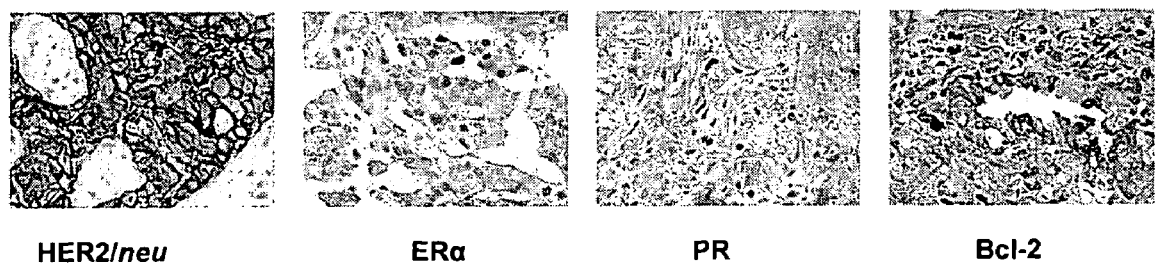
HER2/neu       ERα       PR       Bcl-2

FOXO3a Levels In Cells with and without GW2974 Treatment

Anti-FOXO3a  
Cell Signaling

Anti-FOXO3a  
Abcam

1=BT474 cells untreated  
2=BT474 cells + GW  
3=AU565 cells untreated  
4=AU565 cells + GW Figure 21
Pre-Treatment
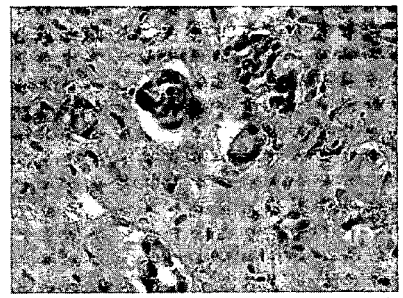
H&E
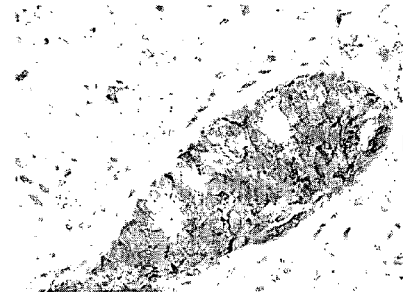
HER-2
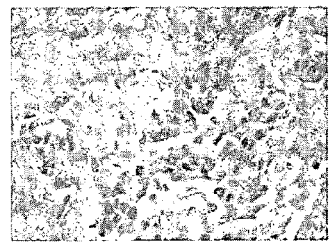
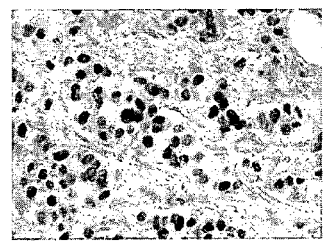
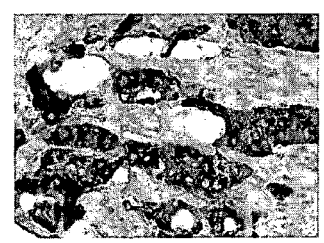
ER　　　　　PR　　　　　Bcl-2
Post-Treatment
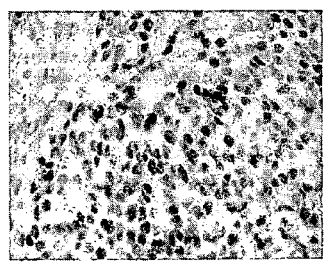
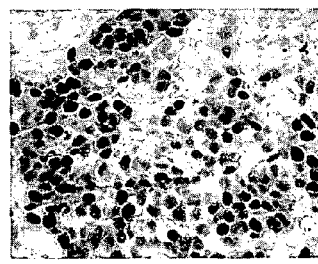
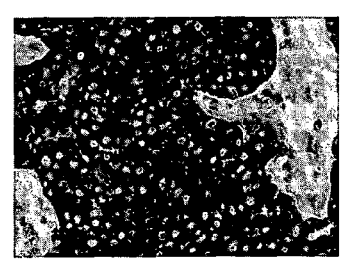

Figure 22
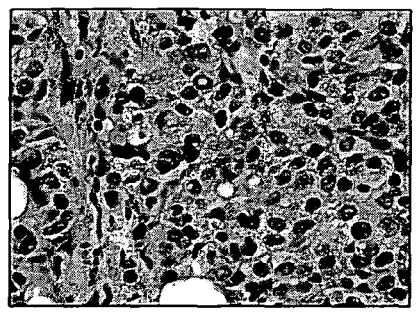
H&E
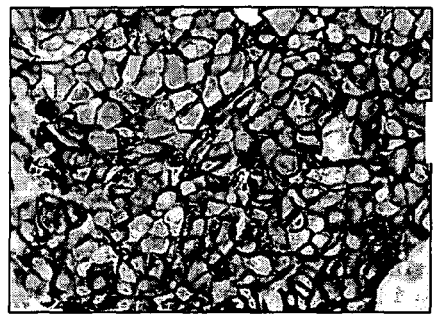
HER-2
Pre-Treatment
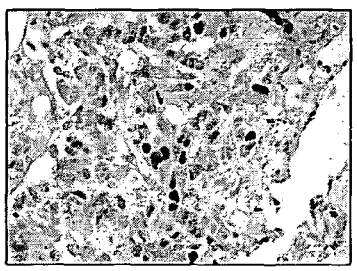
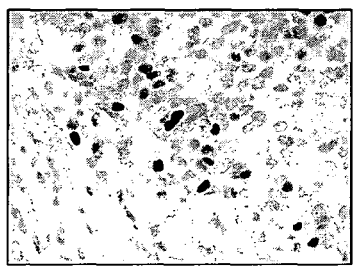
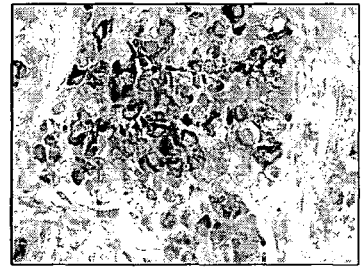
ER　　　　　　　　　PR　　　　　　　　　Bcl-2
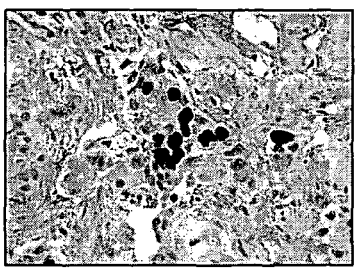
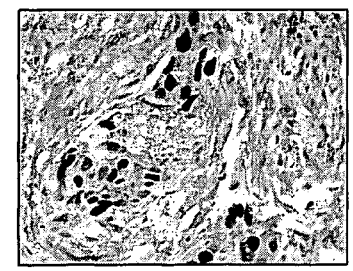
Post-Treatment

Figure 23
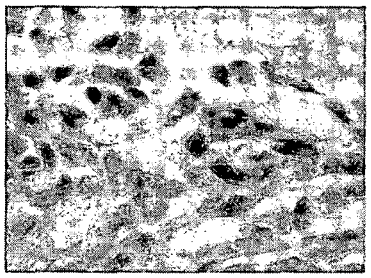
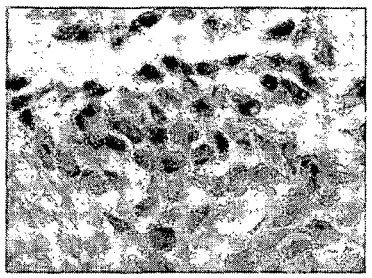
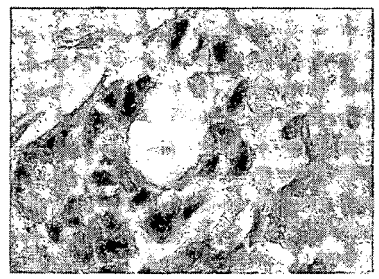
ER Before
Treatment
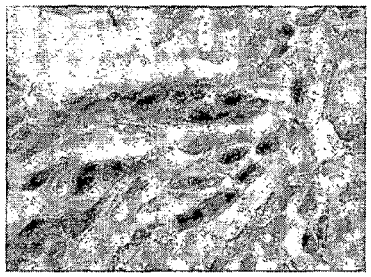
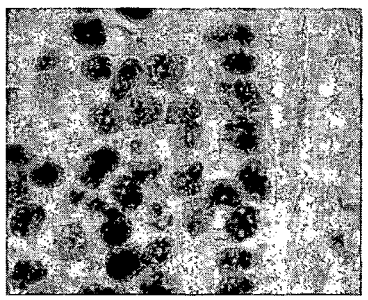
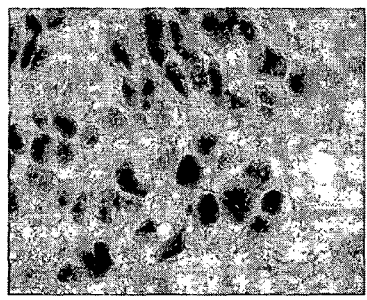
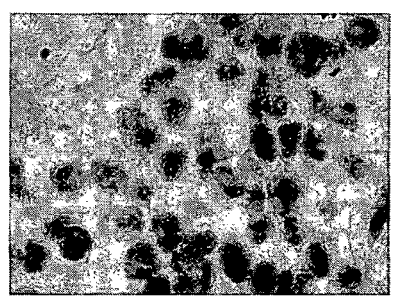
ER After
Treatment Figure 25
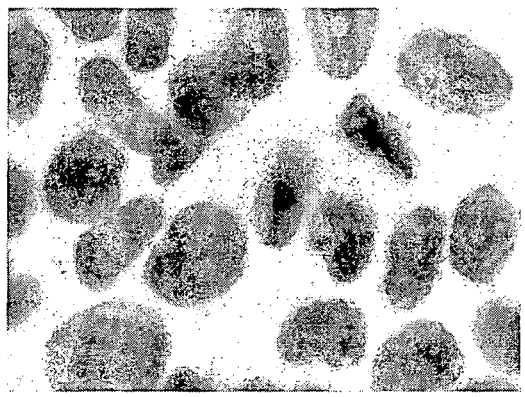 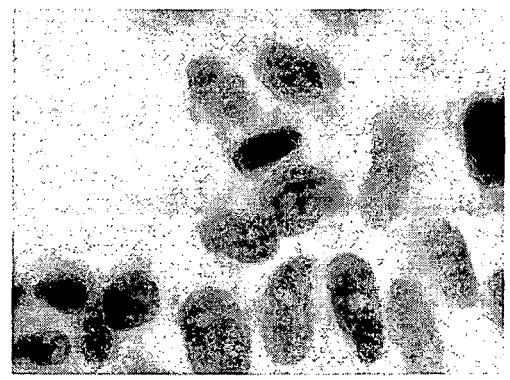
UNTREATED
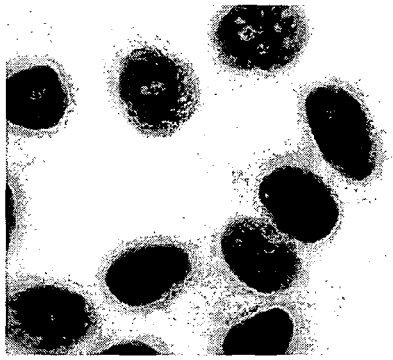 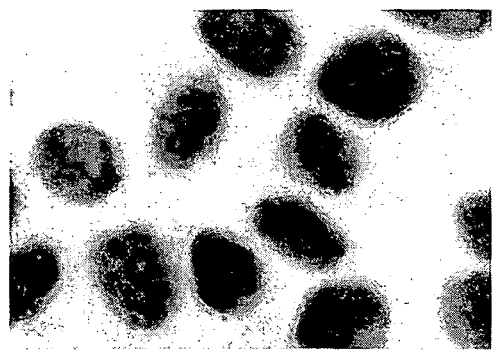
TREATED WITH GW-2974

METHODS AND MATERIALS FOR PREDICTING RESPONSIVENESS TO TREATMENT WITH DUAL TYROSINE KINASE INHIBITOR

This application claims priority to U.S. Provisional Patent Application Ser. No. 60/635,198 filed 10 Dec. 2004, the entire contents of which are incorporated herein by reference.

BACKGROUND

1. Technical Field

The present invention relates to the use of a panel of targeted therapy markers in selecting which anti-cancer treatment or therapy to use in a particular subject.

2. Background Information

Over 8,000,000 persons in the United States have been diagnosed with cancer, a leading cause of death in the United States. By 2001, cancer accounted for 22.9% of all deaths in the United States. Men in the United States have a 1 in 2 risk of developing cancer, while women in the United States have a 1 in 3 risk.

Cancer is a disease of accumulation of clonal cells due to abnormal cell proliferation. Accumulated clonal cells are generally referred to as a tumor. It is the increase in tumor cell number, and thus tumor burden, which ultimately accounts for the adverse effects on the host. The goal of most current cancer treatments is to reduce the number of tumor cells and to prevent their further accumulation. Thus, cancer treatments are targeted therapies.

For example, cancer may be treated by surgery, which involves the bulk removal of cancerous tissue. Though surgery may be effective in removing localized tumors found at certain locations such as in the breast, colon, or skin, it cannot be used in the treatment of tumors located in other areas, such as the backbone, nor can it be used in the treatment of disseminated neoplastic conditions such as leukemia.

Radiation therapy is another current method for treating cancer. Radiation therapy involves the exposure of living tissue to ionizing radiation causing death or damage to the exposed cells, including both those that are tumor cells and those that are not. Chemotherapy may also be used to treat cancer. Chemotherapy involves the use of chemical agents to disrupt cell replication or cell metabolism. It is used most often in the treatment of breast, lung, and testicular cancer. Currently there is a broad variety of therapeutic agents that may be used in the treatment of human cancer. Many, however, have debilitating adverse side effects.

Of these debilitating adverse side effects nausea and vomiting are the most common and severe. Other adverse side effects include cytopenia, infection, cachexia, mucositis in patients receiving high doses of chemotherapy with bone marrow rescue or radiation therapy; alopecia (hair loss); cutaneous complications, such as pruritis, urticaria, and angioedema; neurological complications; pulmonary and cardiac complications in patients receiving radiation or chemotherapy; and reproductive and endocrine complications. Radiation and chemotherapy-induced side effects significantly impact the quality of life of the patient and may dramatically influence patient compliance with treatment. If severe, many of these adverse effects may lead to hospitalization, or require treatment with analgesics for the treatment of pain.

Although some success has been achieved with the current methods of treating cancers, such approaches continue to be limited by a fundamental inability to accurately predict the likelihood of a clinically successful outcome. This is particularly true with regard to the sensitivity or resistance of a particular patient's tumor to a particular treatment or therapeutic agent. The inability to accurately predict the likelihood of a clinically successful outcome is problematic because of the adverse effects associated with cancer treatments and therapeutic agents.

Given the significant occurrence of cancer in the population and the severe adverse effects associated with current cancer treatments, there is a need for practical assays to predict the likelihood of individual tumor sensitivity to cancer treatment, including sensitivity to particular therapeutic agents. Such assays would permit the choice of a treatment or therapeutic agent or some combination thereof that a particular patient's cancer is likely to be sensitive to. The ability to predict clinical outcome of any given cancer treatment or therapeutic agent would enable health care givers to select treatments that will optimize the long-term treatment of a particular cancer, while avoiding the toxic effects of treatments that are ineffective. Thus, there is a need in this art for developing panels of targeted therapy markers, which will aid those of ordinary skill in the art in predicting the clinical effectiveness of anticancer treatments and therapeutic agents.

There also is a current need in the art for clinically focused microarrays that can be used both as an exploratory device in drug development and as a predictive diagnostic tool for determining which patients are most likely to benefit from a particular therapy. There is a need for a microarray platform, with proven predictive assays, that can be used and interpreted in a clinical pathology laboratory. Most microarray platforms are not designed to be highly automated and cannot be used by technologists without a high degree of skilled training.

BRIEF SUMMARY

Therefore, in one example, the present invention is a method of using a panel of targeted therapy markers to select a treatment that is likely to result in a clinically positive outcome for a particular subject.

In another example, the present invention is a method of using a panel of targeted therapy markers to predict the likelihood that a particular treatment will result in a clinically positive outcome.

In one example, the present invention may be or involve using a panel of targeted therapy markers which are cellular receptors that play a role in tumorigenesis.

In another example, the present invention may be or involve use of a panel of targeted therapy markers which are ligands to cellular receptors that play a role in tumorigenesis.

Another example of the present invention may be or involve a panel of targeted therapy markers which are molecules that function in programmed cell death.

In a further example, the present invention may be or involve use of a panel of targeted therapy markers which are some combination of cellular receptors that play a role in tumorigenesis, ligands to those cellular receptors, and molecules that function in programmed cell death.

In another example, the present invention is a microarray comprising a panel of targeted therapy markers, wherein the targeted therapy markers are cellular receptors that play a role in tumorigenesis, ligands to cellular receptors that play a role in tumorigenesis, molecules that function in programmed cell death or some combination thereof. In one aspect, the microarray comprises twenty or fewer targeted therapy markers. In another aspect, the microarray comprises ten or fewer targeted therapy markers.

In a further example, the present invention is a microarray comprising targeted therapy markers for epidermal growth factor receptor (EGFR) (also called ErbB1), ErbB2 (also called HER2/neu), ErbB3, ErbB4, insulin-like growth factor-1 receptor (IGF-1R), neu differentiation factor (NDF) (also called heregulin), transforming growth factor-α (TGF-α), estrogen receptor (ER), progesterone receptor (PR), and Bcl-2.

BRIEF DESCRIPTION OF THE DRAWINGS

FIG. 1 is a schematic illustrating targeted therapy markers that might be used in a panel of such markers for each of breast tumors and non-breast tumors.

FIG. 2 illustrates immunohistochemistry (IHC) staining, done in part with hematoxylin and eoisin (H&E), of targeted therapy markers present in a tissue sample from a subject. In particular, FIG. 2 illustrates IHC staining of a panel of targeted therapy markers including, erbB2, IGF-1R, NDF, EGFR, TGF-α, ER, PR, Bcl-2, and RhoB. This patient responded positively to treatment with a dual tyrosine kinase inhibitor.

FIG. 3 is a series of photographs of tumor cells from the BT 474 cell line (ATCC # HTB-20) stimulated with estrogen and (a) untreated; (b) treated with tamoxifen; (c) treated with GW2974 (a dual EGFR/HER2 inhibitor); or (d) treated with GW2974 and tamoxifen. FIG. 3 illustrates that GW2974 increases cell death in the presence of tamoxifen.

FIG. 4 is a series of photographs illustrating that GW2974 upregulates ER (and PR) expression in breast cancer cells.

FIG. 6 illustrates that approximately only 20% of the AU-565 cells treated by GW2974 were viable whereas approximately 50% of the AU-565/Bcl-2 cells treated by GW2974 were viable.

FIG. 8 illustrates that pAkt is not expressed in cells treated with GW2974, and expression of pErk1 and pErk2 is decreased in cells treated with GW2974 relative to baseline control (actin). Further, FIG. 8 demonstrates that GW2974 is not effective at treating cells pre-treated with estrogen.

FIG. 9 illustrates that MCF-7(HER2) cells have lower estrogen response levels than MCF-7 cells.

FIG. 11 is a photograph illustrating showing AU-565 breast cancer cells stained for expression of the forkhead transcription factor 3 (FOXO3A), a pro-apoptotic factor. FIG. 11 illustrates that lapatinib treatment upregulates FOXO3A in AU-565 breast cancer cells.

FIG. 12 is a schematic illustrating the mechanism of response and resistance to ErbB tyrosine kinase inhibitors. FIG. 12(a) illustrates the regulation of FOXO3a, ER, and Bcl-2 in untreated cells while FIG. 12(b) illustrates the regulation of FOXO3A, ER, and Bcl-2 in cells treated by GW2974.

FIG. 14 is a photograph (with 10× magnification ("10×")) of a sample from a patient with invasive breast carcinoma. The sample was treated with GW572016. The photograph shows TUNEL staining of the sample at day 1 (d1) and day 21 (d21) after treatment.

FIG. 16 is a series of photographs showing immunohistochemistry (IHC) staining for various targeted therapy markers in samples obtained from a patient having a HER2/neu overexpressing breast cancer. Samples were obtained from the patient both prior to treatment with a dual EGFR/HER2 inhibitor and after treatment. This patient did not respond to treatment with a dual EGFR/HER2 inhibitor. FIG. 16 illustrates that prior to treatment this patient had low expression levels of ERα, PR, and Bcl-2 while following treatment, this patient had a modest increase in expression levels of ERα and Bcl-2.

FIG. 21 is a series of photographs of breast cancer tissues stained using IHC and showing upregulation of ER following treatment with a dual EGFR/HER2 inhibitor.

FIG. 22 is a series of photographs of breast cancer tissues stained using IHC and showing upregulation of ER following treatment with a dual EGFR/HER2 inhibitor.

FIG. 23 is a series of photographs of breast cancer tissues stained using IHC and showing upregulation of ER following treatment with a dual EGFR/HER2 inhibitor. FIG. 23 also illustrates a change in ER localization in breast cancer tissues treated with lapatinib. In particular, FIG. 23 illustrates that the upregulation of ER is accompanied by ER localization from the cytoplasmic area to the nuclear area.

FIG. 25 is a series of photographs illustrating that treatment with a dual EGFR/HER2 inhibitor causes accumulation of the ER in the cellular nucleus, which indicates that the ER is activated. In particular, FIG. 25 shows MCF-7(HER2) cells that were grown on glass coverslips and treated with 1 mM of GW2974 for 4 days. Nuclei are stained with DAPI and ER is detected by an immunofluorescent antibody

DETAILED DESCRIPTION OF THE DRAWINGS AND THE PRESENTLY PREFERRED EMBODIMENTS

Figure 2:
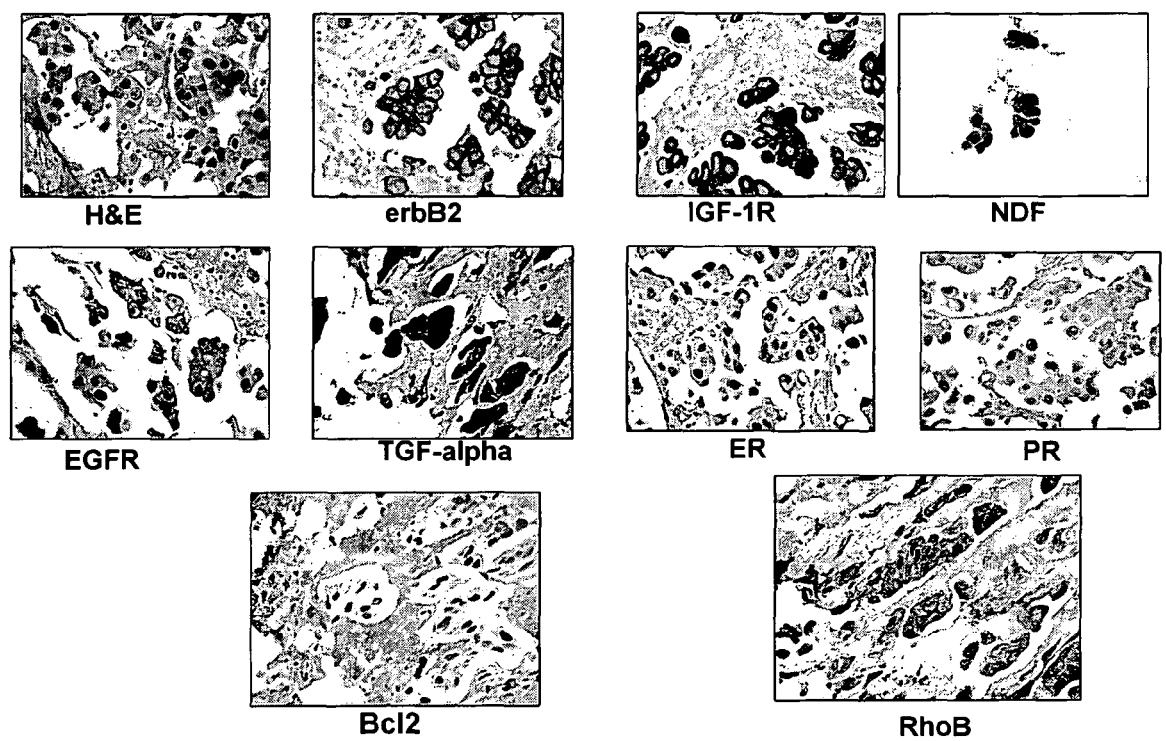
FIG. 2 is a series of photographs of biopsy samples obtained from a single subject.

It is to be understood that this invention is not limited to the particular methodology, protocols, cell lines, animal species or genera, constructs, or reagents described and as such may vary. For example, one of ordinary skill in the art may use RNA or protein changes, or a panel of antibodies for phosphorylated targeted therapy markers. It also is understood that the terminology used herein is for the purpose of describing particular embodiments only, and is not intended to limit the scope of the present invention which will be limited only by the claims.

Unless defined otherwise, all technical and scientific terms used herein have the same meaning as commonly understood to one of ordinary skill in the art to which this invention belongs.

DEFINITION OF THE TERMS

The following definitions are provided in order to aid the reader in understanding the detailed description of the present invention.

As used herein, the singular forms "a," "an," and "the" include plural reference unless the context clearly dictates otherwise. Thus, for example, reference to "a cell" is a reference to one or more cells and includes equivalents thereof known to those skilled in the art, and so forth.

The terms "cancer" and "cancerous" refer to or describe the physiological condition in mammals that is typically characterized by unregulated cell growth. The cells that divide and grow uncontrollably invade and disrupt other tissues and spread to other areas of the body (metastasis) through the lymphatic system or the blood stream. Examples of cancer include but are not limited to, carcinoma, lymphoma, sarcoma, and leukemia. More particular examples of such cancers include prostate cancer, colon cancer, squamous cell cancer, small-cell lung cancer, non-small cell lunar cancer, gastrointestinal cancer, pancreatic cancer, glioblastoma, cervical cancer, ovarian cancer, breast cancer, liver cancer, bladder cancer, hepatoma, colorectal cancer, endometrial carcinoma, salivary gland carcinoma kidney cancer, liver cancer, vulval cancer, thyroid cancer, hepatic carcinoma and various types of head and neck cancer. Cancer exerts its deleterious effect on the body by 1) destroying the surrounding adjacent tissues: e.g. compressing nerves, eroding blood vessels, or causing perforation of organs; and 2) replacing normal functioning cells in distant sites: e.g. replacing blood forming cells in the bone marrow, replacing bones leading to increased calcium levels in the blood, or in the heart muscles so that the heart fails.

"Tumor", as used herein, refers to all neoplastic cell growth and proliferation, whether malignant or benign, and all precancerous and cancerous cells and tissues.

"Treatment," as used herein refers to an intervention performed with the intention of preventing the development or altering the pathology of a disorder. Accordingly, "treatment" refers to both therapeutic and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

"Therapy" as used herein refers to an intervention performed with the intention of preventing the development or altering the pathology of a disorder. "Therapy" refers to various methods that target particular diseases with particular disease fighting agents. For example, a targeted cancer therapy might involve radiation therapy directed at an isolated tumor mass.

The term "inhibitor" refers to a molecule which represses or prevents another molecule from engaging in a reaction, either directly or indirectly. For example, the terms "EGFR inhibitor," "erbB2 inhibitor," "HER1 inhibitor," "HER3 inhibitor," and "HER4 inhibitor" refer to molecules that are able to inhibit EGFR, erbB2, HER1, HER3, and/or HER4 activity and/or expression. The reported EGFR or erbB2 inhibitors include, but are not limited to, lapatinib, trastuzumab, cetuximab, tarceva, and gefitinib. The term "inhibitor" also refers to functional equivalents, analogs, conjugates, and pharmaceutically effective derivatives. "Inhibitor" also includes antibodies to the repressed molecule.

The terms "polypeptide", "peptide", "protein", and the like are used interchangeably herein to refer to any polymer of amino acid residues of any length. The polymer can be linear or non-linear (e.g., branched), it may comprise modified amino acids or amino acid analogs, and it may be interrupted by chemical moieties other than amino acids. The terms also encompass an amino acid polymer that has been modified naturally or by intervention; for example, by disulfide bond formation, glycosylation, lipidation, acetylation, phosphorylation, or any other manipulation or modification, such as conjugation with a labeling or bioactive component.

By "functionality" is meant the ability to function in a manner that is either normal, or sufficiently close to normal that it does not result in a diseased state or a state of higher susceptibility to disease or disorder.

The term "functional equivalent" refers to a compound or a peptide or small molecule that is able to function in a similar manner to compounds disclosed herein. For example, a functional equivalent could be compound that is able to function similarly to EGFR or erbB2 inhibitors. For example, the functional equivalent of EGFR inhibitor could bind and interfere with the functioning of EGF and its role in autophosphorylation of the tyrosine kinase receptor.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "overexpression" refers to a cell having a significantly increased number of functional gene products compared to the average amount of that gene product found in a cell of the same type. Overexpressed gene products can refer to cell receptors, ligand, or any other cellular molecule. For example, overexpression of EGFR and/or erbB2 has been documented in various cancer types including breast (Verbeek et al., *FEBS Letters* 425:145 (1998)); colon (Gross et al., *Cancer Res.* 51:1451 (1991)); lung (Damstrup et al., *Cancer Res.* 52:3089 (1992)); renal cell (Stumm et al., *Int. J. Cancer,* 69:17 (1996), Sargent et al., *J. Urology* 142:1364 (1989)); and bladder (Chow et al., *Clin. Cancer Res.* 7:1957 (2001); Bue et al., *Int. J. Cancer,* 76: 189 (1998); Turkeri et al., *Urology* 51: 645 (1998)). Overexpression may be assessed by any suitable method known in the art, including but not limited to imaging, gene amplification, number of cell surface receptors present, protein expression, and mRNA expression.

The phrase "therapeutically effective" is intended to qualify the amount of therapeutic agent used in the treatment. This amount will achieve the goal of treating, preventing or inhibiting neoplasia or a neoplasia-related disorder.

Neither the term "predictive" nor the term "prognostic" is meant to imply 100% predictive ability. Rather use of these terms indicates that subjects with certain characteristics are more likely to experience a clinically positive outcome than subjects who lack such characteristics. It will be apparent to one skilled in the art that, just as certain conditions are identified herein as associated with an increased likelihood of a clinically positive outcome, the absence of such conditions will be associated with a decreased likelihood of a clinically positive outcome.

The phrase "clinically positive outcome" refers to biological or physical responses to treatments or therapeutic agents that are recognized by those skilled in the art as indicating a slowed or decreased rate of tumor growth, compared to tumor growth that would occur in the absence of any treatment. A "clinically positive outcome" does not necessarily indicate a cure, but could indicate a lessening of symptoms experienced by a subject, an increase in expected or achieved survival time, a decreased or slowed rate of tumor growth, cessation of tumor growth, and/or regression of tumor mass (each as compared to that which would occur in the absence of treatment).

As used herein, "array" or "microarray" refers to an array of distinct polynucleotides, oligonucleotides, polypeptides, or oligopeptides synthesized on a substrate, such as paper, nylon, or other type of membrane, filter, chip, glass slide, or any other suitable solid support. There are several microarrays that are commercially available. For example, Roche Diagnostics manufactures the AmpliChip™ CYP450, which identifies mutations in the cytochrome p450 gene and has the power to identify patients as slow or fast metabolizers of certain drugs. Another example of a diagnostic array that is currently available is the Oncotype™ DX Breast Cancer Assay from Genomic Health. See Paik et al., 2004. *NE J. Med.* 351; 27:2817-2826. This microarray analyzes a panel of 21 genes to predict the likelihood of distant disease recurrence as well as response to chemotherapy in women diagnosed with breast cancer.

In one embodiment, the microarray of the present invention comprises a film-based microarray such as the BioFilmChip™ available from AutoGenomics (Carlsbad, Calif.). This microarray may be used with a platform such as the Infiniti™ Analyzer, also available from AutoGenomics (Carlsbad, Calif.)

In another embodiment, the microarray is prepared and used according to the methods described in U.S. Pat. No. 5,837,832, Chee et al.; PCT application WO95/11995, Chee et al.; Lockhart et al., 1996. *Nat Biotech.,* 14:1675-80; and Schena et al., 1996. *Proc. Natl. Acad. Sci.* 93:10614-619, all of which are herein incorporated by reference in their entirety. In other embodiments, such arrays are produced by the methods described in Brown et al., U.S. Pat. No. 5,807,522. Arrays and microarrays may be referred to as "DNA chips" or "protein chips."

"Therapeutic agent" means any agent or compound useful in the treatment, prevention or inhibition of neoplasia or a neoplasia-related disorder.

The term "condition" refers to any disease, disorder or effect that produces deleterious biological consequences in a subject.

The term "subject" refers to an animal, or to one or more cells derived from an animal. Preferably, the animal is a mammal, most preferably a human. Cells may be in any form, including but not limited to cells retained in tissue, cell clusters, immortalized cells, transfected or transformed cells, and cells derived from an animal that have been physically or phenotypically altered.

"Mammal" for purposes of treatment refers to any animal classified as a mammal, including humans, domestic and farm animals, and zoo, sports, or pet animals, such as dogs, horses, cats, cattle, pigs, sheep, etc. Preferably, the mammal is human.

As used herein "control" refers to a sample obtained from a non-cancerous subject. The "control" exemplifies normal, typical, or standard expression levels of a targeted therapy marker.

The phrase "panel of targeted therapy markers" refers to two or more targeted therapy markers.

Methods for Selecting Cancer Treatments or Therapeutic Agents that are Likely to Result in Clinically Positive Outcomes Although any methods, devices, and materials similar or equivalent to those described herein may be used in the practice or testing of the invention, the preferred methods, devices and materials are now described. This description of embodiments of the invention is illustrative only and is not intended to limit the invention in any manner.

The present invention relates to a panel of targeted therapy markers and methods of using a panel of targeted therapy markers. Targeted therapy markers are molecules that function in the various pathways that control cell growth, proliferation, survival and death. For example, targeted therapy markers are cellular receptors or molecules functioning in the programmed cell death ("PCD") pathway. The expression and activity levels of the panel of targeted therapy markers are useful for assessing and predicting a subject's sensitivity to a particular treatment or therapeutic agent used to treat cancer. Specifically, those of ordinary skill in the art can use the panel of targeted therapy markers to determine the likelihood that a particular therapeutic agent and/or treatment will result in a clinically positive outcome for the subject. In addition, the panel of targeted therapy markers can be used to select a therapeutic agent or treatment or some combination thereof likely to result in a clinically positive outcome.

The utility of the present invention is not limited to a particular cancer, treatment, or therapeutic agent. Instead, the present invention might be used with any cancer. For example, the present invention can be used with cancers expressing tyrosine kinase receptors such as erbB receptors and epidermal growth factor receptors (EGFRs), or with cancers expressing nuclear receptors such as estrogen receptors (ERs) and progesterone receptors (PRs). Such cancers include but are not limited to breast, endothelial, lung, colon, ovarian, prostate, and brain cancers.

While it is not limited to any particular cancers, it is useful to describe the present invention as it relates to breast cancer. Normal breast cells express various cellular receptors including: (1) tyrosine kinase receptors such as erbB receptors and EGFRs and (2) nuclear receptors such as ERs and PRs. Complex interactions between cellular receptors and various ligands that function by binding to or interacting with the cellular receptors regulate the growth, development, and proliferation of breast cells.

When normal receptor-ligand binding relationships or growth control mechanisms within a cell are disturbed, uncontrolled cell division may result. This can lead to tumorigenesis, or cancer. For example, overexpression of cellular receptors often leads to constitutive activation of these receptors (i.e., signaling in the absence of their cognate ligands) and may contribute to the initiation and maintenance of cancer. Cancer then, is a complex disease that is induced and regulated by a variety of cellular activities. Indeed, there is not any known specific sequence of events that leads to or contributes to the development of cancer.

Thus, it is difficult to develop cancer treatments that will be effective in treating a particular cancer. Traditionally, tumor size or progression of disease has been used to determine whether an individual is responding to a particular treatment. However, traditional analyses are conducted after a particular treatment has been initiated or completed. Thus, it is not known whether a particular treatment or therapy will result in a clinically positive outcome until after a patient has undergone that therapy or treatment.

The present invention provides those of skill in the art with the ability to select cancer treatments or therapeutic agents that are likely to result in a clinically positive outcome. In particular, the present invention provides methods for analyzing the expression and activity patterns of various targeted therapy markers in a tissue sample. The targeted therapy markers of the present invention are molecules that function in various cellular signaling pathways.

Multiple cellular signaling pathways are involved in or can lead to cancer. Therefore, it is within the scope of the present invention to analyze patient or tumor samples to precisely determine what pathways are activated or functional. In the present invention, three cellular signaling pathways are particularly important: (1) the cellular signaling pathway involving erbB, EGFR, or other tyrosine kinase receptors; (2) the cellular signaling pathway involving ER, PR, or other nuclear receptors; and (3) the cellular signaling pathway leading to programmed cell death (PCD) or apoptosis.

Although the present invention may be used with a tissue sample, including with RNA or protein extracted from that tissue sample, obtained from subjects currently undergoing a particular treatment or therapy, or who have previously undergone a particular treatment or therapy, an advantage of the present invention is that it can be used before any treatment is initiated or prior to use of any therapeutic agent. Thus, use of the targeted therapy markers of the present invention allows earlier identification of treatments and therapeutic agents likely to result in a clinically positive outcome. In addition, use of the targeted therapy markers of the present invention allows earlier identification of treatments and therapeutic agents that are not likely to result in a clinically positive outcome.

For example, prior to any treatment or use of any therapeutic agent, one of ordinary skill in the art will analyze a panel of targeted therapy markers to determine whether a particular treatment is likely to be effective at treating a particular tumor in a subject. More specifically, one of ordinary skill in the art may analyze the panel of targeted therapy markers for functionality, expression levels and activity levels. The panel of targeted therapy markers analyzed can include targeted therapy markers downstream of each other. If the present invention indicates that a targeted therapy marker is expressed, functioning or active in a manner that deviates from normal expression, function, or activity, or if down stream markers are not activated, one of ordinary skill in the art may conclude that a particular treatment or therapeutic agent is not likely to result in a clinically positive outcome. In such a case, the subject can be offered an alternate treatment, and spared potential side effects of a treatment that is ineffective for their specific tumor.

As used herein, targeted therapy markers should not be confused with the use of disease prognosis markers. Certain molecular markers are known as indicators of more aggressive cancers and are associated with decreased average survival time (compared to subjects whose tumors do no express such markers). The present invention is not directed to general disease prognosis markers, but to the use of targeted therapy markers that are useful in assessing the likely clinical outcome following treatment of a solid tumor with a particular treatment or therapeutic agent. The present invention is intended to aid in identification of subjects who are likely to experience a clinically positive outcome following treatment with a particular therapeutic agent or treatment (compared to the likelihood of such a response in the general population).

Targeted Therapy Markers:

There are many different targeted therapy markers that might be used in practicing the present invention. Some examples of targeted therapy markers are discussed below. Additionally, FIG. 1 illustrates some examples of targeted therapy markers that can be used, for example, in microarrays, in practicing the present invention. The following description of embodiments of the invention is illustrative only and is not intended to limit the invention in any manner.

Cellular Receptors

In one aspect of the present invention, targeted therapy markers are cellular receptors that are targeted in cancer therapies. Specifically, tyrosine kinase receptors, (erbB receptors and EGFRs) and nuclear receptors (ERs and PRs) are examples of targeted therapy markers that may be used in the present invention.

In the present invention, a targeted therapy marker that is a cellular receptor may be analyzed for activity and expression levels. For example, quantification of expression levels of various tyrosine kinase cellular receptors in human breast cancer specimens has been shown to provide valuable information on tumor aggressiveness, prognosis, and sensitivity to treatment.

There are numerous tyrosine kinase receptors that can be used as targeted therapy markers in the present invention. Generally, tyrosine kinase receptor classes I-V are well known in the art. Tyrosine kinase receptors comprise an extracellular domain containing a ligand binding site, a single hydrophobic transmembrane α-helix, and a cytosolic domain that includes a region with protein-tyrosine kinase activity. Receptor class is mainly determined by the structural characteristics of the extracellular domain of the receptor because intracellular portions of tyrosine kinase receptors share high degrees of similarity. Due to structural differences in the extracellular domains, the different receptor classes possess different ligand binding properties and specificities. (Hubbard, *Prog. Biophys. Mol. Biol.*, 71:343-358 (1999)).

The EGFR family of tyrosine kinase receptors, class I receptors, is one example of a group of targeted therapy markers that might be used in the present invention. The EGFR family of receptors includes erbB1 (EGFR or HER1), erbB2 (HER2), erbB3, and erbB4. These receptor tyrosine kinases are widely expressed in epithelial, mesenchymal, and neuronal tissues where they play a role in regulating cell proliferation, survival, and differentiation. (Sibilia and Wagner, *Science*, 269:234 (1995); Threadgill et al., *Science*, 269: 230 (1995)).

In one example of practicing the present invention, erbB2 is a targeted therapy marker and the expression levels of erbB2 are measured. Overexpression of erbB2 is associated with a positive clinical outcome following treatment with trastuzumab or lapatinib. In contrast, overexpression of erbB2 with expression of IGFR (insulin-like growth factor receptor) is associated with a negative clinical outcome following treatment with an EGFR/erbB inhibitor. (Smith, Bacus et al., *Br. J. Cancer,* 91(6):1190-4 (2004)). Therefore, expression levels of an erbB2 and/or an IGFR targeted therapy marker(s) can be used to identify potentially successful cancer treatments or therapeutic agents.

EGFR and erbB3 are further examples of targeted therapy markers that can be used in the present invention. In particular, cellular signaling cascades involving the erbB3 receptor and EGFR can lead to activation of the erbB2 receptor. Activated erbB2 receptor in turn activates the Erk and PI3K/Akt pathways, which promote cell survival. Activation of pathways promoting cell survival may impair the effectiveness of a cancer treatment or therapeutic agent. Thus, in one aspect, the present invention is a panel of erbB2, erbB3, EGFR, Erk, and PI3K/Akt targeted therapy markers. One of ordinary skill in the art may therefore obtain a tissue sample from a subject and analyze the activity and expression levels of this panel of targeted therapy markers. The results of that analysis can be used by one of ordinary skill in the art to select treatments and therapeutic agents likely to result in clinically positive outcomes.

Overexpression of erbB2 in breast cancer cells is driven by AP-2 transcription factors. However, transcription of erbB2 is repressed by oestrogen in human breast cancer cells. In particular, oestrogen expression down-regulates the expression of AP-2 proteins, but does not affect the activity of AP-2 proteins. Constitutive expression of AP-2β or AP-2γ, but not AP-2α, abrogates the estrogenic repression of erbB2. (Perissi et al., *Oncogene,* 19:280-88 (2000)). Thus, oestrogen, AP-2α, AP-2β, and AP-2γ are further examples of targeted therapy markers that can be included in a panel of such markers in practicing the present invention.

Figure 5:
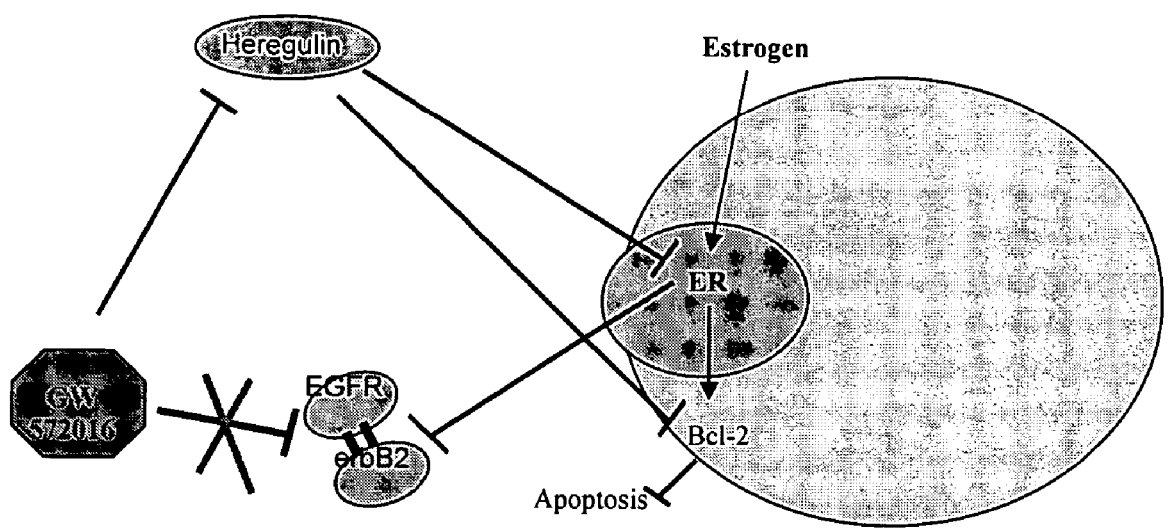
FIG. 5 is a schematic illustrating the pathway through which ER positive tumors reduce the efficacy of small molecule inhibitors of erbB receptor tyrosine kinase activity. In this pathway, high levels of ER expression downregulate erbB2 expression. Heregulin ("HRG") signaling normally results in inhibition and downregulation of ER. But when erbB2 expression is downregulated, the inhibitory effect of HRG (via erbB2) on ER is reduced.
Figure 8:
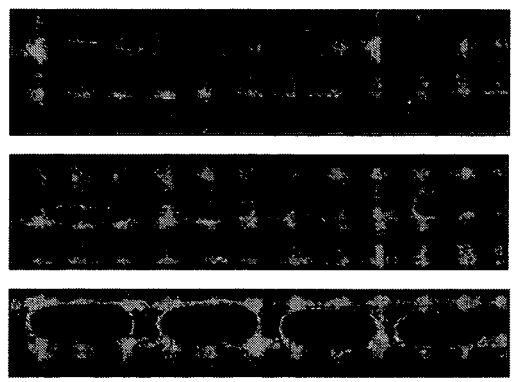
FIG. 8 is a photograph showing the results of a western blot of MCF-7+HER2 cells. This photograph illustrates expression patters for pErk1/Erk2/pAkt and actin for (1) untreated cells, (2) cells treated with estrogen, (3) cells treated with GW2974, and (4) cells pre-treated with estrogen followed by treatment with GW2974.
Figure 9:
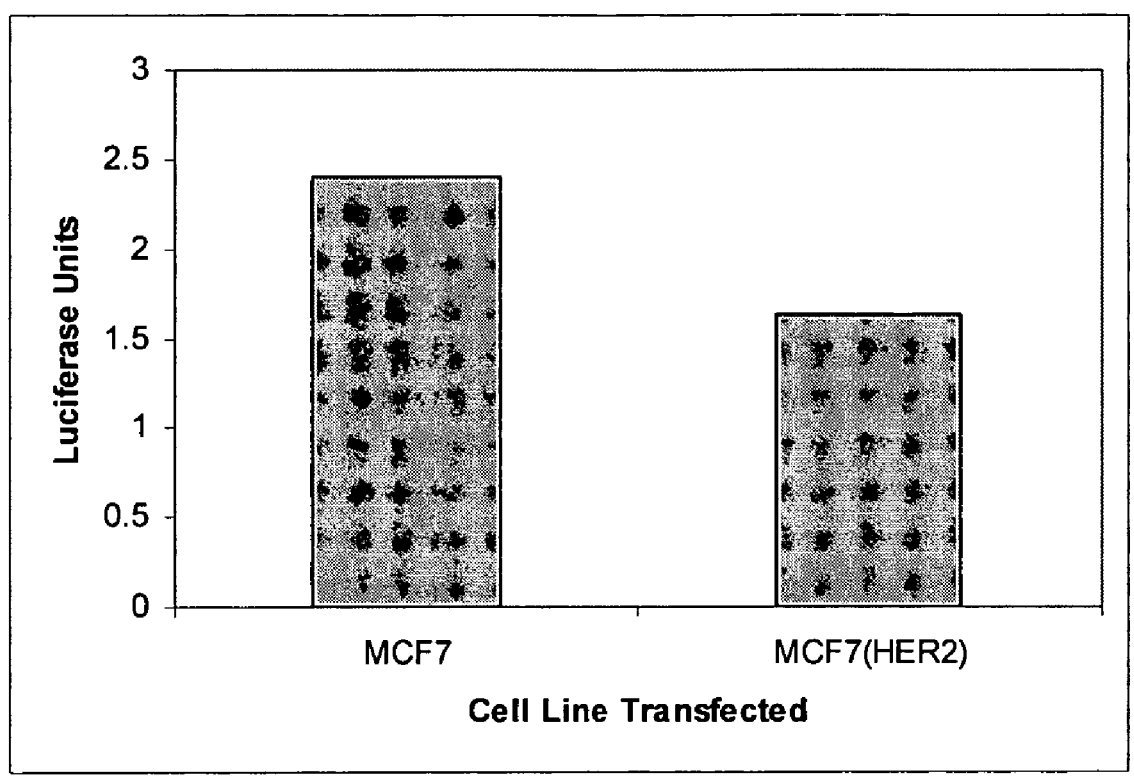
FIG. 9 is a bar graph illustrating estrogen responsive luciferase reporter expression in MCF-7 and MCF-7(HER2) cells.

Nuclear cellular receptors, such as ER and PR, are also examples of targeted therapy markers that can be included in a panel of such markers. Significantly, there is an inverse correlation between erbB2 receptor expression and ER expression. (Perissi et al., *Oncogene,* 19:280-88 (2000)). In particular, as illustrated by FIG. 5, the signaling pathway that is activated by erbB2 expression, down-regulates ER expression. Further, as shown in FIG. 9, MCF-7 and MCF-7(HER2) cells transfected to express an estrogen responsive luciferase reporter gene demonstrate that the MCF-7(HER2) cells have much lower estrogen response levels than MCF-7 cells. Even further, FIG. 8 illustrates that pAkt protein expression in MCF-7(HER2) cells is greatly reduced following treatment with a dual EGFR/HER2 inhibitor such as GW2974. However, FIG. 8 also illustrates an increase in expression of pAkt in cells treated with GW2974 that had first been pre-treated with estrogen. Thus, increased levels of the ER targeted therapy marker indicate that treatments targeting erbB2 would not be likely to result in a clinically positive outcome. Similarly, cancer treatments and therapeutic agents that target ER are not likely to result in a positive clinical outcome if a tissue sample analyzed in accordance with the present invention has increased expression levels of the targeted therapy marker erbB2.

Tumor expression of ER-α is considered indicia that endocrine therapies, such as the antiestrogen tamoxifen, will result in a clinically positive outcome. (Murphy et al., *Clin. Cancer Res.,* 10:5902-5906 (2004)). However, some tumors expressing ER-α do not respond to endocrine therapies and other tumors acquire resistance to these therapies. Thus, ER-α expression alone is not a sufficient targeted therapy marker.

There are several different phosphorylation sites on ER-α that may modulate ER action. (Murphy et al., *Clin. Cancer Res.,* 10:5902-5906 (2004)). For example, phosphorylation of ER-α at serine 118 (pER-α(Ser118)) plays a role in ER-α transcription activation. Thus, pER-α(Ser118) is another example of a targeted therapy marker that can be used in the panel of such markers in practicing the present invention. For example, a panel of targeted therapy markers might include ER and pER-α(Ser118). Expression of pER-α(Ser118) indicates a functional, ligand-dependent ER signaling pathway. Thus, expression of both ER and pER-α(Ser118) is indicia of a positive clinical outcome following treatment with endocrine therapies such as tamoxifen.

In addition, a mitogen-activated protein kinase (MAPK) pathway is involved in the phosphorylation of ER-α. MAPK pathways transduce a large variety of external signals, leading to a wide range of cellular responses, including growth, differentiation, inflammation and apoptosis. Therefore, MAPK is another targeted therapy marker that can be included in a panel of targeted therapy markers used in practicing the present invention.

Many nuclear receptors (NR) other than ER may be used as targeted therapy markers in the present invention. NRs are a superfamily of ligand activated transcription factors that modulate specific gene expression. Currently there are over 100 nuclear receptors identified. They are categorized into steroid receptor subfamilies: Class I NR, which are ligand dependent and capable of homodimerization and Class II NR, which are ligand independent and capable of both homo- and heterodimerization. (Klinge, C M. "Estrogen receptor interaction with co-activators and co-repressors." *Steroids.* 2000. 65(5):227-51). Some examples of Class I NR are glucocorticoid receptor, mineralocorticoid receptor, progesterone receptor, androgen receptor and estrogen receptor. Some examples of Class II NR are retinoic acid receptor, retinoid x receptor, vitamin D receptor, thyroid receptor, and peroxisome proliferation activated receptor.

Ligands

In another aspect of the present invention, the panel of targeted therapy markers includes ligands that bind to cellular receptor targeted therapy markers. Ligand targeted therapy markers may also be used in a panel that does not include cellular receptor targeted therapy markers.

Some examples of ligands that might be used in the present invention are growth factors, hormones, or other molecules that bind or interact with cellular receptors. Ligands used as targeted therapy markers in the present invention include but are not limited to estrogen, estradiol (E2), progesterone, androgen, glucocorticoid, prolactin, thyroid hormone, insulin, fibroblast growth factors (FGFs), EGF, transforming growth factor alpha (TGF-α), and heregulin (HRG) (also known as gp30).

Ligand binding to a cellular receptor may activate the receptor or initiate a signal transduction cascade. For example, binding between a growth factor and its cognate receptor molecule might initiate a complex signal transduction cascade that involves sequential phosphorylation-dephosphorylation reactions. Such signal transduction cascades mediate the biological effects of growth factors on cell growth and differentiation. (Saceda et al., *Endocrinology,* 137(10): 4322-4330 (1996)).

A family of peptide ligands, including EGF, Neu Differentiation Factor (NDF), HRG, and transforming growth factor α (TGF-α), regulate erbB and EGF receptor signaling. (Salomon et al., *Crit. Rev. Oncol. Hematol.,* 19:183 (1995)). Specifically, ligand binding of either receptor induces homo- and heterodimerization of the receptor. This, in turn, leads to receptor autophosphorylation and activation (Graus-Porta et al., *EMJO J.,* 16:1647 (1997); Tzahar et al., *Mol. Cell. Biol.,* 16:5276 (1996)). ErbB2 is the preferred heterodimeric partner for EGFR, erbB3, and erbB4. Although a number of soluble ligands have been identified for these three receptors, none has been identified for erbB2, which seems to be trans-activated following heterodimerization.

With the exception of erbB3, all erbB receptor family members share a highly conserved cytoplasmic tyrosine kinase domain. Autophosphorylation of specific cytoplasmic tyrosine residues establishes binding sites for Src-homology 2 (SH2) and phosphotyrosine-binding-domain containing proteins that in turn link to downstream effectors involved in cell proliferation (MAPK or Erk1/2) and survival (PI3K/AKT) pathways. Thus, in one aspect, the present invention is a panel of targeted therapy markers which are ligands that bind erbB receptors and EGFRs and activate cell proliferation and survival pathways.

For example, HRG can be used as a targeted therapy marker in the present invention. HRG is also referred to as gp30. HRG activates tyrosine kinase receptors, and thereby initiates signal-transduction cascades involved in cellular responses such as proliferation and differentiation. In particular, HRG induces tyrosine phosphorylation, and hence activation, of the EGFR and erbB2 receptors. HRG treatment of breast cancer cells also induces activation of cellular survival and proliferation pathways including those pathways involving Erk/MAP kinases, Jnk/SAP kinases, and PI3k/Akt. (Balana et al., *Oncogene,* 18:6370-79 (1999)). Thus, in one aspect of the present invention, HRG, Erk/MAP kinases, Jnk/SAP kinases, and PI3k/Akt are a panel of targeted therapy markers that are assayed for activity levels. If these ligands or pathways are activated, then a treatment or therapeutic agent directed at inhibiting these pathways could be used to increase the likelihood of a positive clinical outcome.

Two members of the receptor tyrosine kinase class I family, erbB3 and erbB4, mediate HRG functions. EGFR, erbB1, and erbB2 are co-receptors for HRG. (Balana et al., *Oncogene,* 18:6370-79 (1999); Pinkas-Kramarski et al., 1997.) In fact, erbB2 is a critical component in mediating HRG-induced breast cancer cell growth. Specifically, if erbB2 is not available to form a heterodimer complex with other members of the erbB family, then HRG activity is blocked and cell growth is decreased. Thus, in cells overexpressing erbB2 receptors, at low concentration HRG induces cell growth, while at high concentrations HRG inhibits cell proliferation. (Saceda et al., *Endocrinology,* 137(10):4322-4330 (1996)). Therefore, in another aspect of the present invention, HRG, EGFR, erbB2, erbB3 and erbB4 can be included in a panel of targeted therapy markers. Including these targeted therapy markers in the panel being analyzed can provide valuable information about the ability of HRG to function in cellular signaling activities.

HRG expression is also relevant to ER expression and endocrine therapies. In particular, HRG expression down-regulates ER expression by inhibiting ER transcription. This regulation of ER expression occurs independently of erbB2 and erbB4 expression levels in the cells. Additionally, constitutive expression of HRG contributes to breast cancer cells progressing from a hormone-dependent phenotype, where ER plays a significant role, to a hormone-independent phenotype. The hormone-independent phenotype is generally associated with an increase in malignancy. (Muller et al., *Biochem. and Biophys. Res. Comm.,* 217(3):1271-1277 (1995)). HRG can also modulate ER activity by decreasing the binding of the ER to ligands commonly referred to as estrogen-response-elements ("EREs"). Therefore, in another aspect, the panel of targeted therapy markers of the present invention, includes HRG, ER, and erbB2 and may include various EREs. The expression and activity levels of these targeted therapy markers provide important information regarding the effectiveness of a hormone treatment or therapy for a particular subject.

Another ligand targeted therapy marker of the present invention, insulin-like growth factor-1 receptor (IGF-1R) is required for HRG proliferative effects in cancer cells. (Balana et al., *Oncogene,* 18:6370-79 (1999)). Higher levels of IGF-1 are associated with increased risk of several cancers. (Lu et al., *Reports—J. of Nat'l Cancer Institute,* 93(24):1852-1857 (2001)). In particular, IGF-1R activation stimulates signaling pathways involved in mitogenesis and cell survival. (Lu et al., *Reports—J. of Nat'l Cancer Institute,* 93(24):1852-1857 (2001)).

IGF-1R signaling is propagated through erbB2. Thus, elevated co-expression of IGF-1R and erbB2 favors formation of erbB2/IGF-1R complexes whose signaling can be blocked by a potent erbB2 kinase inhibitor such as lapatinib, trastuzumab, or gefitinib. Conversely, in the absence of elevated erbB2 expression, IGF-1R activates the cellular survival pathway, PI3K/Akt. Indeed, higher levels of IGF-1R are known to reduce the ability of trastuzumab and gefitinib to inhibit the growth of breast cancer cells overexpressing erbB2. (Lu et al., *Reports—J. of Nat'l Cancer Institute,* 93(24):1852-1857 (2001)).

Thus, in practicing the present invention, panels of targeted therapy markers that include IGF-1R molecules will provide information useful in determining the most effective treatment protocols. For example, a panel of targeted therapy markers can include IGF-1, IGF-II, IGFBPs, IGFBP proteases, PTEN, erbB2, EGFR, ER, PR, HRG, and Bcl2. This panel of markers will provide one of ordinary skill in the art with important information because trastuzumab resistance is associated with overexpression of IGF-I or IGF-II, underexpression of growth-inhibitory IGFBPs, overexpression of IGFBP proteases, or reduced activity of intracellular phosphatases, such as PTEN, that normally limit IFG-I signaling. (Lu et al., *Reports—J. of Nat'l Cancer Institute,* 93(24):1852-1857 (2001)).

Another example of a targeted therapy marker that can be used in the present invention is P70 S6 kinase protein (PS6). PS6 is a significant predictor of regional recurrence of breast cancer following primary treatment for early-stage breast cancer. The protein product of PS6, activates the translation initiation machinery in response to growth factor stimulation of its upstream regulator, TOR. Thus, PS6 plays an important role promoting cellular proliferation and can function as a targeted therapy marker in the present invention.

Survivin is another example of a molecule that can be used as a targeted therapy marker in the present invention. Overexpression of survivin is common in tumorigenesis and progression of breast carcinoma. Survivin is associated with inhibition of apoptosis and functions by blocking caspase activation. (Dabrowski et al., 2004. *Folia Histochem Cytobiol.* 42(3):169-172). In particular, survivin inhibits the function of caspase-3 and caspase-7. High survivin concentrations are associated with ER and PR negative tumors. (Span et al., 2004. *Clin. Chem.* 50(11):1986-93).

E2 or 17β-estradiol is another ligand that might be used as a targeted therapy marker in the present invention. E2 is an estrogen that controls cell proliferation in normal breast cells by inducing expression of immediate and delayed hormone-responsive genes important for cell cycle progression. (Perillo et al., *Mol. and Cell. Biol.,* 20(8):2890-2901 (2000)). However, factors which stimulate cellular proliferation have interplay with molecular mechanisms that control programmed cell death (PCD). PCD is induced by a variety of stimuli and inhibited by the Bcl-2/Ced-9 family of proteins.

Figure 6:
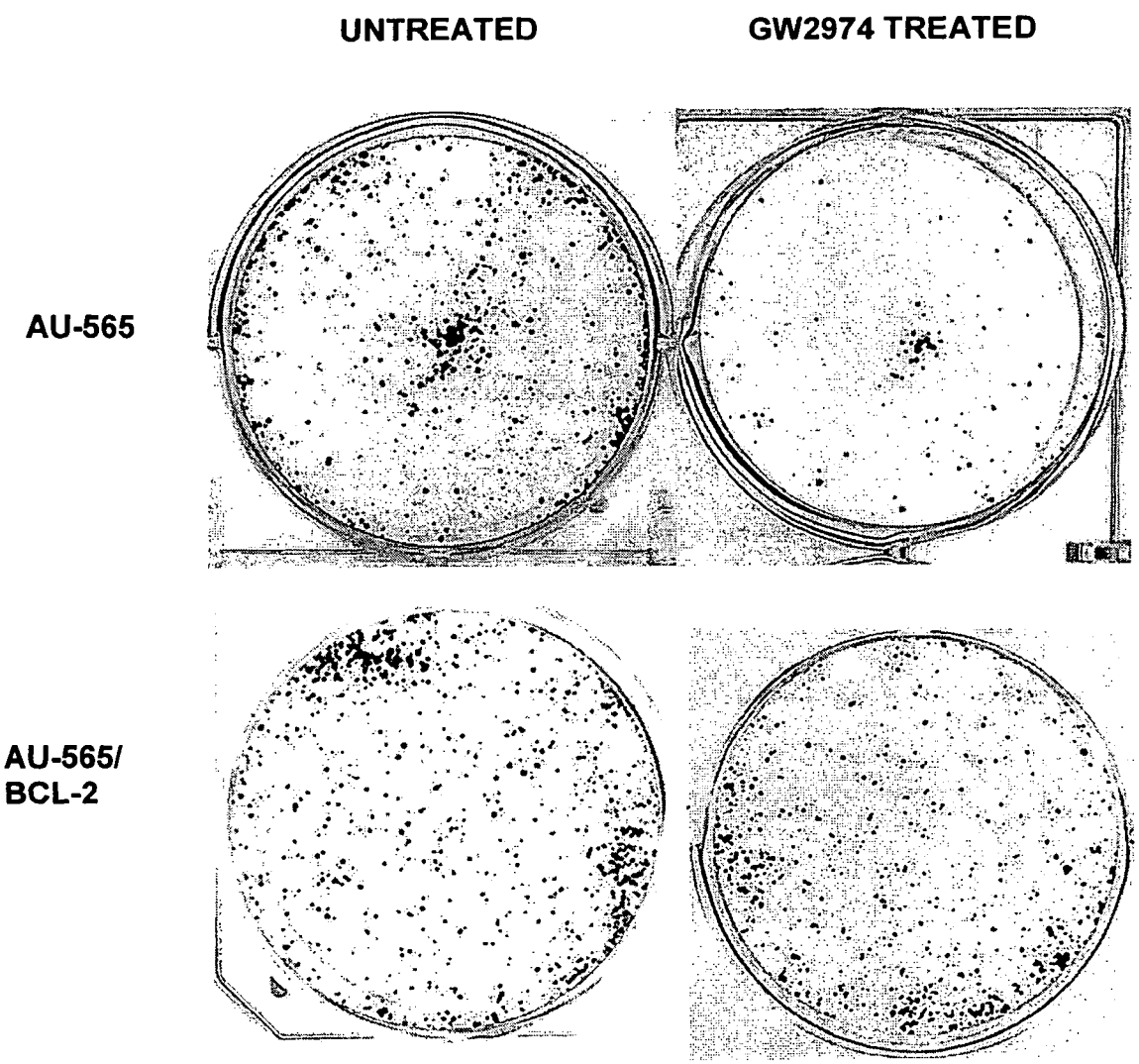
FIG. 6 is a photograph demonstrating that after transfection with the Bcl-2 gene, AU-565 cells overexpressing Bcl-2 are more resistance to treatment with the dual EGFR/HER2 inhibitor, GW2974. In particular

In fact, Bcl-2 has been shown to prevent apoptosis after several treatments including treatment with hydrogen peroxide. (Perillo et al., *Mol. and Cell. Biol.*, 20(8):2890-2901 (2000)). E2 upregulates bcl-2 transcription, which is mediated via phosphorylation of CREB by PKA, wherein PKA is activated by cAMP signal. E2 generates the cAMP signal via a G-protein-coupled receptor, GPR30. (Kanada et al., *J. Investigative Dermatology*, 121(6):100-09 (2003)). Thus, GPR30/E2 mediated Bcl-2 expression is associated with apoptosis resistance and can therefore function as a targeted therapy marker in the present invention. Indeed, FIG. 6 illustrates that breast cancer cells having high expression levels of Bcl-2 had a significantly higher (approximately 30%) rate of cell survival following treatment with GW2974. See also FIG. 4, which demonstrates that GW2974 upregulates ER (and PR) expression in breast cancer when treated with E2.

Similar to its function in up-regulating bcl-2 transcription, E2 inhibits, via ER activity, the time-dependent increases in Bak (a molecule that promotes apoptosis) mRNA and protein. (Leung et al., *Cancer Letters*, 124:47-52 (1998)). Thus, E2, which can be included in a panel of targeted therapy markers, is an important marker because of its role in regulating expression and activity of various molecules that function in the PCD pathway.

PCD and Apoptotic Molecules

Figure 13:
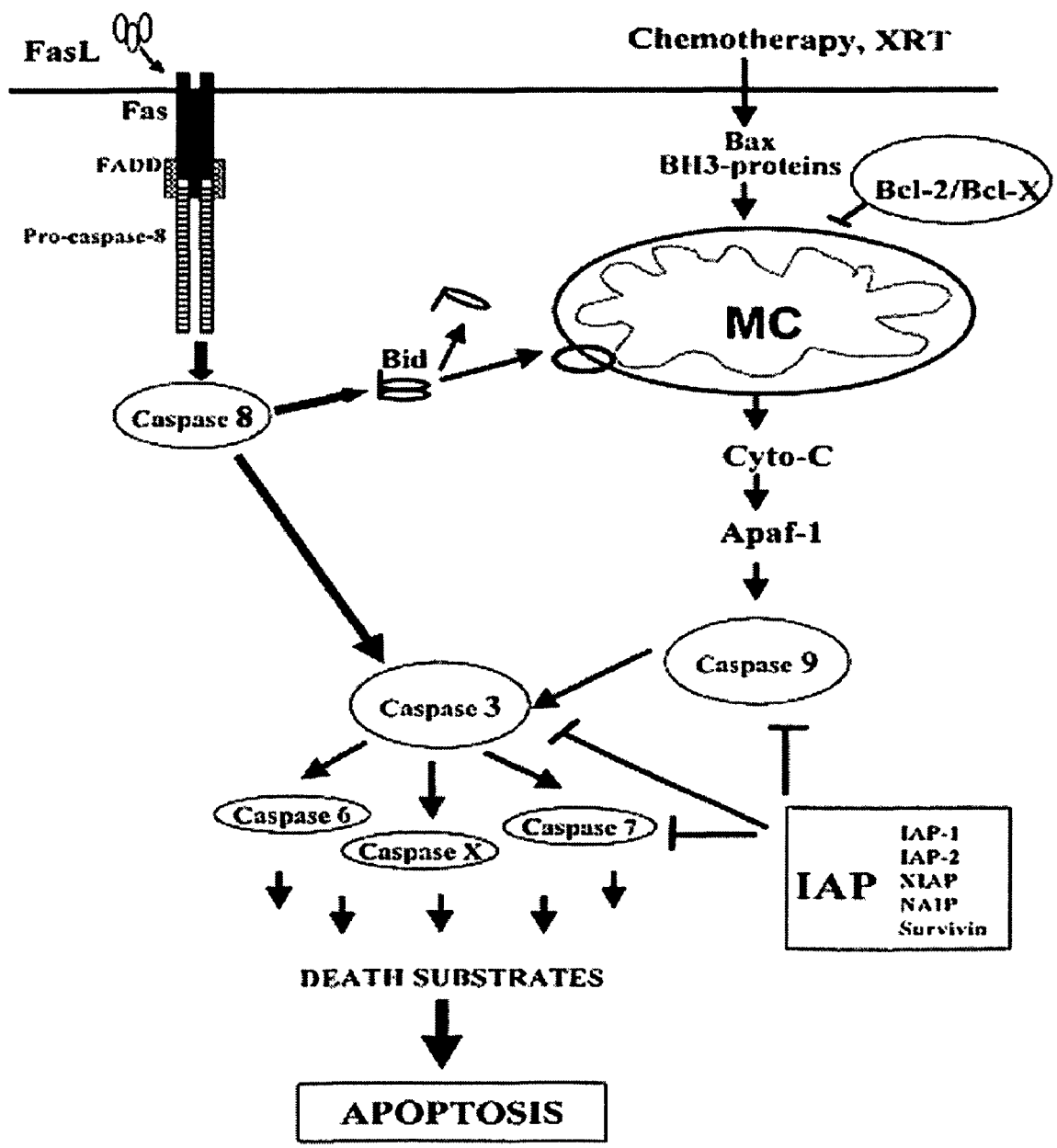
FIG. 13 is a schematic illustrating the mitochondrial and death receptor pathways to apoptosis.

In a further aspect, the present invention is a panel of targeted therapy markers that includes molecules that play a role in PCD as targeted therapy markers. Alternatively, the panel of targeted therapy molecules of the present invention includes only molecules that play a role in PCD. The targeted therapy markers may play a role in either the mitochondrial or death receptor pathway to apoptosis, or may play a role in both. FIG. 13 is a schematic illustrating various targeted therapy makers that function in the mitochondrial and death receptor pathways to apoptosis Cancer or tumorigenesis can disable PCD through various mechanisms (Makin, *Expert Opin. Ther. Targets*, 6:73 (2002); Johnstone et al., *Cell*, 108:153 (2002)), which can lead to extended cell survival and may contribute to neoplastic cell expansion. The goal of most cancer treatments and therapeutic agents is to cause death of the cancer cell. Therefore, molecules the function in PCD are important targeted therapy markers because defects in apoptotic pathways confer resistance to treatments and targeted therapies including, chemotherapy, radiation therapy, and immune-mediated cell destruction.

In particular, resistance of breast cancer cells to treatment with chemotherapeutic agents is linked to bcl-2 expression in those cells. (Dong et al., *J. Biol. Chem.*, 274(45):32099-32107 (1999)). Thus, in one aspect of the present invention, bcl-2 expression levels might be used as a targeted therapy marker.

The Bcl-2 family of proteins consists of both inhibitors and promoters of the mitochondrial pathway of PCD. There are four important Bcl-2 structural homology motifs: BH1, BH2, and BH3, present in both the anti- and pro-survival subfamilies, and BH4, present only among antiapoptotic proteins. (L. Gibson, S. P. Holmgreen, and D. C. Huang, et al. Bcl-w, a novel member of the bcl-2 family, promotes cell survival *Oncogene* 1996. 13: 665-675). Most apoptotic proteins contain BH1 and BH2, and those closely resembling Bcl-2 contain all four domains. The proapoptotic proteins form two subfamilies. The Bax group includes Bax, Bak, and Bok, resembles Bcl-2, and contains BH1, 2, and 3 domains. The BH3 domain group encompasses seven family members (Bik, Blk, Hrk, BNIP3, BimL, Bad, Bid, EGL-1) that possess only the BH3 domain, which is essential for their function.

Many Bcl-2 family proteins can associate with each other through a complex network of homo- and heterodimers that depend on interactions between the BH1, BH2, or BH3 domains. (T. W. Sedlak, Z. N. Oltvai, and E. Yang, et al. Multiple Bcl-2 family members demonstrate selective dimerizations with Bax *PNAS* 1995. 92: 7834-7838). Bcl-2 forms homodimers or heterodimers with Bax, Bcl-XL, Bcl-Xs, Mcl-1, and BAD. The ratio of antiapoptotic versus proapoptotic dimers is important in determining resistance of a cell to apoptosis. Thus, in practicing the present invention, a panel of targeted therapy markers can include, for example, bcl-2, Bax, Bak, Bad, Bok, Bik, Blk, Hrk, BNIP3, BimL, Bid, and EGL-1.

In particular, analyzing Bcl-2 and Bax expression and activity levels, is important because the degree of protection Bcl-2 provides against apoptosis correlates with the amount of Bcl-2 that is free of Bax. (Otter, S., et al. The binding properties and biological activities of Bcl-2 and Bax in cells exposed to apoptotic stimuli *J Biol Chem* 1998. 273: 6110-6120).

Another example of a molecule that can be used in the present invention as a targeted therapy marker because of its role in PCD is forkhead transcription factor 3 (FOXO3A). As shown in FIG. 11, FOXO3A is upregulated by treatment with the dual EGFR/HER2 inhibitor, lapatinib, which leads to an increase in cell death. FIG. 12 illustrates the mechanism of response and resistance to ErbB tyrosine kinase inhibitors, such as lapatinib and GW2974.

Other examples of molecules that can be used in the present invention as targeted therapy markers because of the roles they play in tumorigenesis, PCD, and drug resistance are listed in Table I.

TABLE I

Summary of the Roles of PCD Initiators, Regulators, or Executioners in Tumorigenesis, PCD, and Drug Resistance

| PROTEIN | ROLE IN TUMORIGENESIS, PCD, AND DRUG RESISTANCE | REFERENCES |
|---|---|---|
| | Tumor Suppressor | |
| p53 | Mutated or altered expression in many cancers. Initiates the mitochondrial PCD pathway. p53 −/− cells are resistant to drug induced apoptosis. | Vogelstein et al., 2000 |
| p19ARF | Mutated or altered expression in many cancers. Blocks MDM2 inhibition of p53. Enhances drug induced apoptosis by p53. | Sherr and Weber, 2000 |
| Rb | Mutated in some cancers, and functionally disrupted in many cancers. Inhibits E2F-mediated transcription. Loss of Rb function induces p53-dependent and independent apoptosis | Harbour and Dean, 2000 |

TABLE I-continued

Summary of the Roles of PCD Initiators, Regulators, or Executioners in Tumorigenesis, PCD, and Drug Resistance

| PROTEIN | ROLE IN TUMORIGENESIS, PCD, AND DRUG RESISTANCE | REFERENCES |
|---|---|---|
| PTEN | Mutated or altered expression in cancers. Regulates Akt activation and subsequence phosphorylation of Bad. Loss of PTEN results in resistance to many apoptotic stimuli. | Di Cristofano and Pandolfi, 2000 |
| Apaf-1 | Mutated and transcriptionally silenced in melanoma and leukemia cell lines. Necessary for activation of caspase-9 following cytochrome c release. Apaf-1 −/− cells are chemoresistant. | Soengas et al., 2001 |
| CD-95/Fas | Mutated and down-regulated in lymphoid and solid tumors. Initiates the death receptor PCD pathway. Loss of function is associated with resistance to drug-induced cell death. | Muschen et al., 2000 |
| TRAIL-R1/R2 | Mutated in metastatic breast cancers. Mutations lead to suppression of death receptor PCD. | Shin et al., 2001 |
| Caspase-8 | Gene silenced in neuroblastomas. Activates both extrinsic and intrinsic apoptotic pathways. Silencing results in resistance to drug-induced apoptosis. | Teitz et al., 2000 |
| Forkhead Box 03A (FOXO3A) Oncogene | Transcription factor that triggers apoptosis by inducing the expression of genes that are critical for cell death. | Liu et al., 2005 |
| MDM2 | Overexpressed in some tumors. Negative regulator of p53. Inhibits drug-induced p53 activation. | Sherr and Weber, 2000 |
| IAPs | Frequently overexpressed in cancer. Down regulation of XIAP induces apoptosis in chemoresistant tumors. | Deveraux and Reed, 1999 |
| NF-kB | Deregulated activity in many cancers. Transcriptionally activates expression of anti-apoptotic members of the Bcl-2 and AIP families. Can inhibit both the death receptor and mitochondrial PCD pathways and induce drug resistance. | Baldwin, 2001 |
| Myc | Deregulated expression in many cancers. Induces proliferation in the presence of survival factors, such as Bcl2, and apoptosis in the absence of survival factors. Can sensitize cells to drug-induced apoptosis. | Evan and Vousden, 2001 |
| Akt | Frequently amplified in solid tumors. Phosphorylates Bad. Hyperactivation induces resistance to a range of apoptotic stimuli including drugs. Also known as protein kinase B or PKB. Akt is a serine/threonine kinase that prevents apoptosis. | Datta et al., 1999; Science 1997, 275: 628-630 |
| P13K | Overexpressed or deregulated in some cancers. Responsible for activation of Akt and downstream phosphorylation of Bad. Inhibition of P13K enhances chemotherapeutic drug-induced apoptosis. | Roymans and Slegers, 2001 |
| Ras | Mutated or deregulated in many cancers. Activates P13K and downstream pathways. Induces cell proliferation and inhibits c-myc and drug-induced apoptosis. | el-Deiry, 1997 |
| FLIP | Overexpressed in some cancers. Prevents activation of caspase-8 and apoptosis induced by some chemotherapeutic agents. | Tepper and Seldin, 1999 |

Subject Samples

The samples used in the present invention include biological samples obtained from a subject of interest and include but are not limited to tumor tissue samples, samples of tissue surrounding or in the vicinity of a tumor, cells including whole cells, cell fractions, and cell extracts, and body fluid samples, such as blood samples. Biological samples may be freshly excised, fixed on a slide using known methods, or cryopreserved.

Preferably the sample is a biopsy, and is suitably sized so that it may be divided into a plurality of portions for testing with one or more putative agents, at one or more concentrations. While a sample may be maintained for up to several days in a suitable maintenance medium, it is preferred to analyze a sample for functionality, expression or activation of targeted therapy markers within about 24 hours or less from the time it is excised.

In addition, for tissue biopsies, it is contemplated to mince or otherwise culture vessels having viable, malignant cell growth from the biopsy as primary cultures. In this way, the number of malignant cells obtainable for use in an assay method of the invention may be multiplied.

Methods of Assessing Functionality, Expression and Activity of Targeted Therapy Markers Those of ordinary skill in the art will appreciate that there are many different methods that can be used to assess the functionality, expression and activity of targeted therapy markers. For example, functionality, expression and activity levels may be determined by immunohistochemistry, a staining method based on immunoenzymatic reactions uses monoclonal or polyclonal antibodies to detect cells or specific proteins, such as cellular receptors. Typically, immunohistochemistry protocols include detection systems that make the presence of markers visible (to either the human eye or an automated scanning system), for qualitative or quantitative analyses. Various immunoenzymatic staining methods are known in the art for detecting a protein, such as a cellular receptor, of interest. For example, immunoenzymatic interactions can be visualized using different enzymes such as peroxidase, alkaline phosphatase, or different chromogens such as DAB, AEC, or Fast Red. IHC staining results may be quantitatively or qualitatively evaluated based on, for example, optical density measurements. For example erB2 optical density can be measured. Optical density (OD) values of <10, 10-15, >15 roughly correlate with 1+, 2+, 3+ in the HercepTest standards, respectively. HercepTest standards are valuable control correlation standards because Hercept-Test is an FDA approved method of determining erbB2 overexpression.

Some other examples of methods that can be used in the present invention to assess the functionality, expression and activity of targeted therapy markers include protein arrays, protein chips, cDNA microarrays or RNA microarrays. More specifically, one of ordinary skill in the art will appreciate that in one example, a microarray may comprise the following genes as targeted therapy markers: EGFR (ErbB1), HER2/neu (ErbB2), ErbB3, ErbB4, NDF (Heregulin), TGF-α, IGF-1R, Estrogen Receptor alpha (ERα), Progesterone Receptor (PR), and Bcl-2. One of ordinary skill in the art also will appreciate that each of these targeted therapy markers serves a different function based on the expression characteristics of each marker in relation to treatment with different therapies. For example, Table II, set forth below, identifies particular functions of targeted therapy markers that may be included in a microarray of targeted therapy markers.

TABLE II

| Gene Name | Targeted Therapy Marker Function |
| --- | --- |
| EGFR (ErbB1) | Predicts response to EGFR inhibitors |
| HER2/neu (ErbB2) | Predicts response to HER2/neu inhibitors |
| ErbB3 | Predicts resistance to EGFR and HER2/neu inhibitors |
| ErbB4 | Predicts resistance to EGFR and HER2/neu inhibitors |
| NDF (Heregulin) | Predicts resistance to EGFR and HER2/neu inhibitors |
| TGFα | Predicts response to EGFR and dual EGFR/HER2 inhibitors |
| IGF-1R | Predicts resistance to certain ErbB inhibitors (e.g. HERCEPTIN ®) but not others (e.g. Lapatinib) |
| Estrogen Receptor alpha (ERα) | High levels prior to treatment predict resistance to ErbB inhibitors |
| Progesterone Receptor (PR) | High levels prior to treatment predict resistance to ErbB inhibitors |
| Bcl-2 | High levels prior to treatment predict resistance to ErbB inhibitors |

The targeted therapy markers of the present invention may be analyzed using any suitable method or system, as will be apparent to one skilled in the art, including those of immunohistochemistry, automated systems, quantitative IHC, semi-quantitative IHC and manual methods. Various automated sample processing, scanning and analysis systems suitable for use with immunohistochemistry are available in the art. Such systems may include automated staining and microscopic scanning, computerized image analysis, serial section comparison, digital report generation, and archiving and tracking of samples. Cellular imaging systems are commercially available that combine conventional light microscopes with digital image processing systems to perform quantitative analysis on cells and tissues, including immunostained samples. (See e.g. the CAS-200 System (Becton, Dickinson & Co.)).

The skilled artisan will appreciate that there are many additional methods that might be used to assess functionality, expression or activity level of targeted therapy markers. Some other examples of methods that might be used in the present invention are discussed in the examples section of this patent. Other examples that might be used in the present invention are western blotting, immunoprecipitation, fluorescence in situ hybridization (FISH), and enzyme immunoassays.

In addition to analyzing a tissue sample for activation of a targeted therapy marker, the present invention contemplates that a skilled artisan may analyze a tissue sample to determine whether a cellular receptor or molecule of interest is degraded in the sample. Cellular receptors occasionally are internalized and degraded by the cell. Western blotting, cDNA microarray, protein chip, immunohistochemistry, FISH, and enzyme immunoassays are some examples of assays that might be used in the present invention to analyze a tissue sample for degradation of a molecule of interest.

Cancer Treatments

Analysis of the targeted therapy markers of the present invention enables those of ordinary skill in the art to assess the sensitivity of a particular tumor or patient to a particular treatment or therapeutic agent. Presently, there are numerous cancer treatments and therapeutic agents. Some treatments are cancer specific, while other may be used with a variety of cancers. For example, many attempts have been made to develop therapeutically active monoclonal antibodies (mAbs) and kinase inhibitors that target either EGFR or erbB2 receptor, for the treatment of numerous types of cancers. More specifically, a number of small molecule, dual EGFR-erbB2 tyrosine kinase inhibitors have been identified and their pre-clinical anti-tumor activities have been reported. (Fry et al., *Proc Natl Acad Sci USA.*, 95:12022 (1998); Cockerill et al., *Bioorganic Med. Chem. Letts.*, 11:1401 (2001); Rusnak et al. *Cancer Res.*, 61:7196 (2001); Rusnak et al., *Mol. Cancer Therap.*, 1:85 (2001)).

Therapeutic agents generally are specific for a certain class of receptor. For example, lapatinib (GW572016) is a cancer treatment that is specific for class I tyrosine receptors. More specifically, lapatinib is a tyrosine kinase inhibitor that blocks activation of both EGFR and erbB2 by inhibiting autophosphorylation of EFGR or erbB2 in tumor cell lines that overexpress either receptor. Lapatinib also interrupts downstream activation of Erk1/2 MAP kinases and P13K/AKT. (Rusnak et al., *Mol. Cancer Therap.*, 1:85 (2001)). In addition, lapatinib has been shown to inhibit signal transduction in EGF-stimulated tumor lines that did not overexpress EGFR. The chemical name of lapatinib is N-{3-chloro-4-[(3-fluorobenzyl)oxy]phenyl}-6-[5-({[2-methylsulfonyl)ethyl]amino}methyl)-2-furyl]-4-quinazolinamine ((WO 99 35146, Carter et al.); a ditosylate form is disclosed in WO 02 02552 (McClure et al.)).

Trastuzumab (Herceptin®), another example of a therapeutic agent, is a tyrosine kinase inhibitor. Trastuzumab is a humanized anti-erbB2 monoclonal antibody that has been approved for the treatment of breast cancers that either overexpress erbB2, or that demonstrate erbB2 gene amplification (Cobleigh et al., *J. Clin. Oncol.*, 17:2639 (1999)). Trastuzumab treatment produces the best clinical outcome in patients whose tumors express high levels of erbB2. Individuals who do not have high levels of erbB2 do not respond well to trastuzumab treatment.

Gefitinib (IRESSA® or ZD1839) is another anti-EGFR targeted approach that is currently undergoing clinical investigation. (See Ranson et al., *Exp. Rev. Anticancer Ther.* 2:161 (2002)). Gefitinib targets class III tyrosine kinase receptors and in particular, targets EGFR. Generally, gefitinib functions by preventing phosphorylation or activation of EGFR, thereby shutting down signaling via this protein and choking the growth of cancer cells. Iressa® is currently in clinical trials for use in treating non-small cell lung cancer.

PKC412 (STI571) and Imitinib (GLEEVEC®) are class III tyrosine kinase inhibitors. Specifically, PKC412 binds to FLT3 receptors and inhibits autophosphorylation of these receptors. Imitinib targets the BCR-ABL oncogene found in CML, as well as mutated forms of the class III tyrosine kinase c-kit, found frequently in gastrointestinal stomach tumors (GIST) (Weisberg, et al., *Cancer Cell,* 1:433-443 (2002)).

Tamoxifen (NOLVADEX®; AstraZeneca Pharmaceuticals, Wilmington, Del.) is an example of an endocrine therapy used to treat cancers. In particular, tamoxifen works by inhibiting the effects of estrogen binding in breast cancer cells. It is often called an "anti-estrogen." This means that tamoxifen reduces or stops the action of estrogen. Under normal circumstances when estrogen comes into contact with the ER on breast cancer cells, it activates the cancer cells to divide so that the tumor grows. Tamoxifen imitates the action of estrogen and fits into the receptor but does not activate the cells to divide. Tamoxifen remains in place and prevents estrogen from reaching the cancer cells so that they either grow more slowly or stop growing altogether. Fasladex and Arinadex are further examples of endocrine therapies used to treat cancers.

Figure 7:
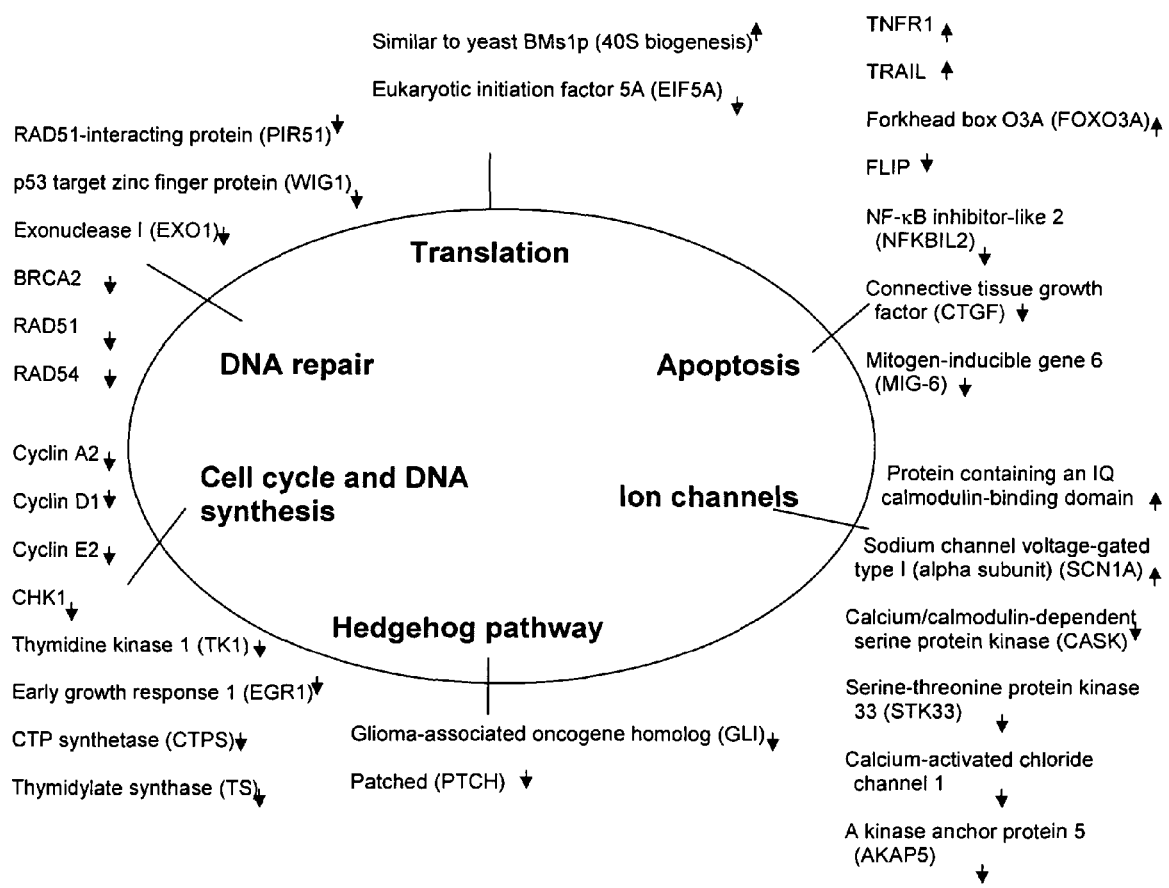
FIG. 7 is a schematic illustrating the classes of gene and modes of regulation by GW2974 treatment.

GW2974 (commercially available from Sigma-Aldrich, St. Louis, Mo. as product number G 0668) is a novel, dual epidermal growth factor receptor protein tyrosine kinase inhibitor. GW2974 blocks the phosphorylation of a peptide substrate by either the EGFR or the ErbB-2 kinase domain. It has been demonstrated that GW2974 exhibits greater than 75-fold selectivity in inhibiting cell growth of breast, gastric, and head/neck carcinoma cell lines compared to normal human foreskin fibroblasts (HFF). The classes of genes regulated by GW2974 treatment are illustrated in FIG. 7.

The above examples of therapeutic agents are not intended to limit the invention in any way. For example, one of skill in the art will appreciate that there are many other therapeutic agents, including others that target tyrosine kinase receptors, such as EGFR. Such other therapeutic agents and treatments are within the scope of the present invention. The present invention can also be used with cancer treatments and therapeutic agents other than those directed to inhibition of tyrosine kinase receptors.

For example, in addition to inhibiting FTL3 receptors, PKC412 downregulates the P13/Akt survival pathway. Inhibition of this pathway by PKC412 is relevant for sensitization to ionizing radiation, an alternative cancer treatment. (Tenzer, A. et al., "The Phosphatidylinositide 3'-kinase/Akt Survival Pathway is a Target for the Anticancer and Radiosensitizing Agent PKC412, and Inhibitor of Protein Kinase C," 2001. Cancer Res. 61:8203-10).

Thus, those of ordinary skill in the art will be able to use information known and available in the art to determine how a particular treatment or therapeutic agent functions. Using the methods and assays of the present invention, along with the targeted therapy markers of the present invention, those of ordinary skill in the art will be able to select treatments and therapeutic agents that are likely to result in clinically positive outcomes, and also will be able to predict the likelihood of achieving a clinically positive outcome using a particular treatment or therapeutic agent.

Figure 10:
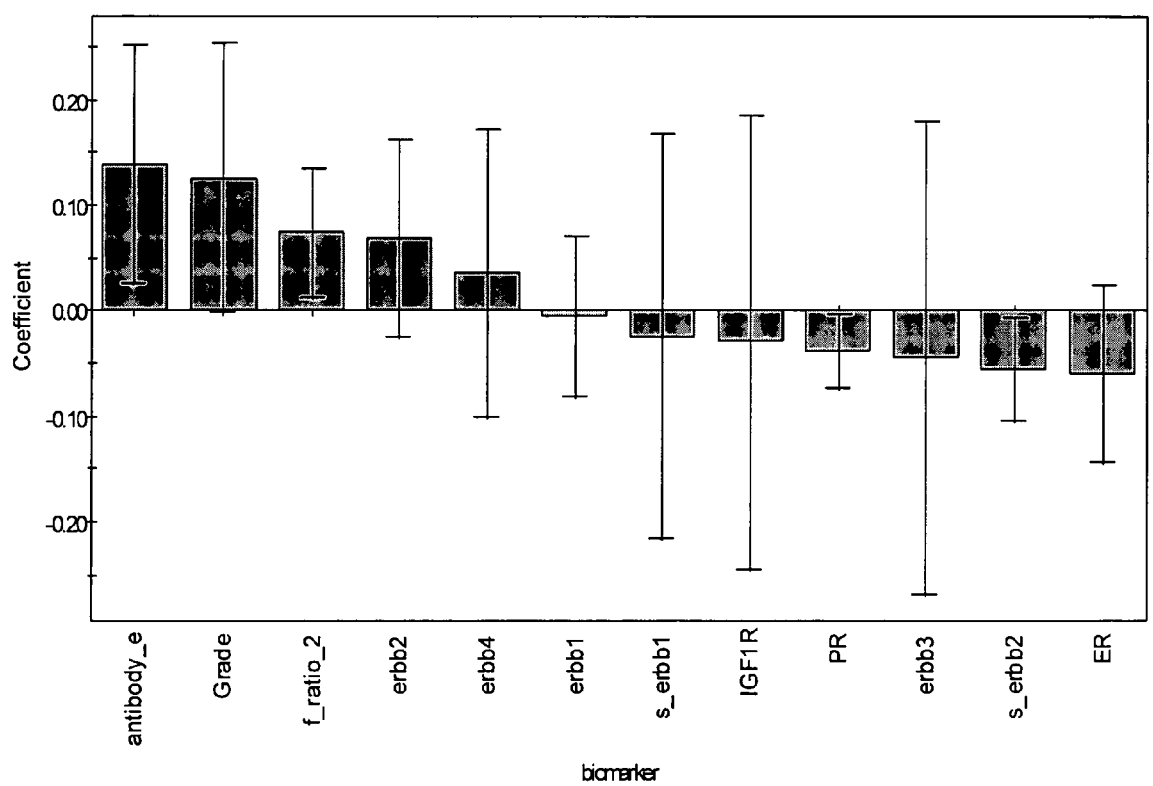
FIG. 10 illustrates the correlation between various targeted therapy markers and patient outcome following treatment with a dual EGFR/HER2 inhibitor. Targeted therapy markers with a coefficient>0 are positively correlated with response and targeted therapy markers with a coefficient<0 are negatively correlated with response.

For example, a patient whose tissue samples indicate overexpression of the following targeted therapy markers: ErbB1 (EGFR), ErbB2 (HER2), Heregulin, NDF, and TGF-α, and negative expression of ER and PR, is expected to exhibit a positive response to treatment with a dual EGFR/HER2 inhibitor, such as HERCEPTIN® (Genentech, Inc., San Francisco, Calif.). In another example, a patient whose tissue samples indicate overexpression of HER2 and negative expression of ER, PR, and Bcl-2, is expected to exhibit a positive response to treatment with a dual EGFR/HER2 inhibitor. In a further example, a patient whose tissue samples indicate overexpression of ERα, PR, and Bcl-2 is expected to exhibit resistance to treatment with an ErbB inhibitor, including dual inhibitors of EGFR/HER. One of ordinary skill in the art will appreciate that many other patient profiles can be generated using the information disclosed herein and used in practicing the present invention. See e.g., FIG. 10, which demonstrates a predicted correlation between expression of various targeted therapy molecules and patient outcome following treatment with a dual EGFR/HER2 inhibitor.

It is intended that the foregoing detailed description be regarded as illustrative rather than limiting. The present invention is further illustrated by the following experimental investigations and examples, which should not be construed as limiting. The contents of all references, patents and published applications cited throughout this patent are hereby incorporated by reference herein.

EXAMPLES

Example 1

Panel Assay Involving TGF-α, HRG, IGF-1R, ER, PR, EGFR, erbB2 and Bcl-2 Staining Biopsy samples are obtained from two different subjects with invasive breast carcinomas. Each subject providing a sample is treated, for example with taxotere and a small molecule dual inhibitor of EGFR/erbB2. Biopsies samples are fixed in 10% Neutral Buffered Formalin (NBF) and paraffin-embedded sections are prepared. Hemotoxylin and eosin (H&E) staining are used to confirm the presence of tumor in the biopsy samples. Quantitative immunohistochemistry ("IHC") analysis is performed as described in Bacus, et al., *Analyt Quant Cytol Histol,* 19:316-328 (1997), which is herein incorporated by reference. In addition, EGFR and erbB2 immunostaining are performed using VMSI automated "BenchMark" staining module, also as described in Bacus, et al., *Analyt Quant Cytol Histol,* 19: 316-328 (1997). The VMSI "I-View" detection kit is used for both of the VMSI pre-diluted primary antibodies. TGFα (1:20) is immunostained using the "BenchMark" with I-VIEW detection chemistry. Slides are placed onto the Autostainer (Dako, Carpinteria, Calif.) and the "LSAB2 kit" (Dako) is employed as the detection chemistry. After staining, EGFR, erbB2, IGF-1R, Heregulin, TGFα, ER, PR and Bcl-2 are counterstained manually with 4% ethyl green (Sigma-Aldrich). ErbB2 optical density (OD) values of <10, 10-15, >15 roughly correlate with 1+, 2+, 3+ in the HercepTest standards, respectively. HercepTest standards are valuable control correlation standards because HercepTest is an FDA approved method of determining erbB2 overexpression.

The staining results may show that Subject A is positive for ER, PR, and Bcl-2. In such a case, according to the present invention, Subject A is not likely to achieve a clinically positive outcome following treatment with a dual EGFR/erbB2 inhibitor. Similarly, Subject B may be negative for ER, PR, and Bcl-2, but according to the present invention, Subject B is likely to achieve a clinically positive outcome following treatment with a dual EGFR/erbB2 inhibitor.

Example 2

Validation of Inclusion of Hormone Receptors in a Panel of Targeted Therapy Markers A breast tumor tissue sample obtained from a patient prior to treatment was stained using standard IHC techniques. IHC staining showed increased levels of HER2/neu and negative expression of ERα, PR and Bcl-2, relative to expression levels of HER2/neu, ERα, PR, and Bcl-2 in normal, non-cancerous tissue. See FIG. 16.

The patient responded to therapy using a dual EGFR/HER2 inhibitor (e.g. HERCEPTIN®, Genentech, Inc. (San Francisco, Calif.). A tissue sample was obtained from the same patient following treatment with the dual EGFR/HER2 inhibitor and stained using standard IHC techniques. IHC staining showed increased levels of HER2/neu as well as slightly increased levels of ERα, PR, and Bcl-2. See FIG. 16.

This expression profile validates inclusion of hormone receptors in a panel of targeted therapy markers. Initial ErbB signaling repressed the ER pathway, which explains the decreased levels of ERα, PR, and Bcl-2 seen in the pre-treatment IHC stains. Inhibition of ErbB signaling with a dual EGFR/HER2 inhibitor relieves the repression of the ER signaling pathway, which explains the slight increase in ERα, PR, and Bcl-2 expression levels seen with IHC staining post-treatment. Therefore, hormone receptors and their targets play a role in resistance to ErbB targeted therapies and should be analyzed as part of a panel of targeted therapy markers prior to any treatment decision.

Example 3

Determination of PCD Using TUNEL

Figure 15:
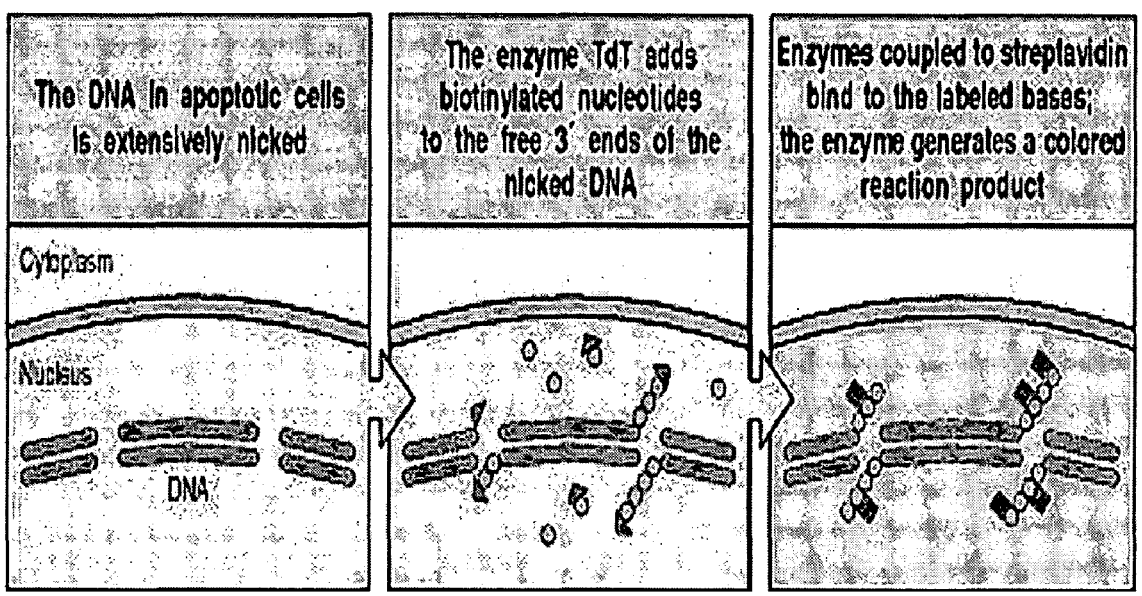
FIG. 15 is a schematic illustrating TUNEL labeling of apoptotic cells.
Figure 17:
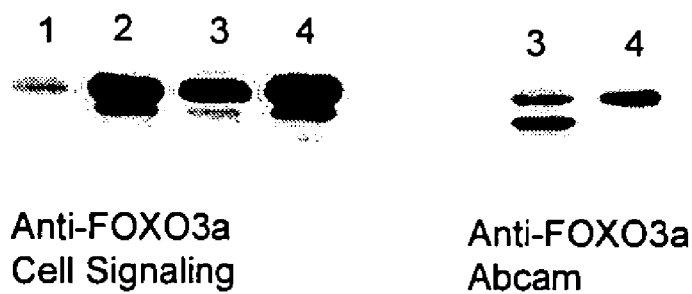
FIG. 17 is a photograph of an ELISA gel showing upregulation of FOXO3 following treatment with lapatinib.
Figure 18:
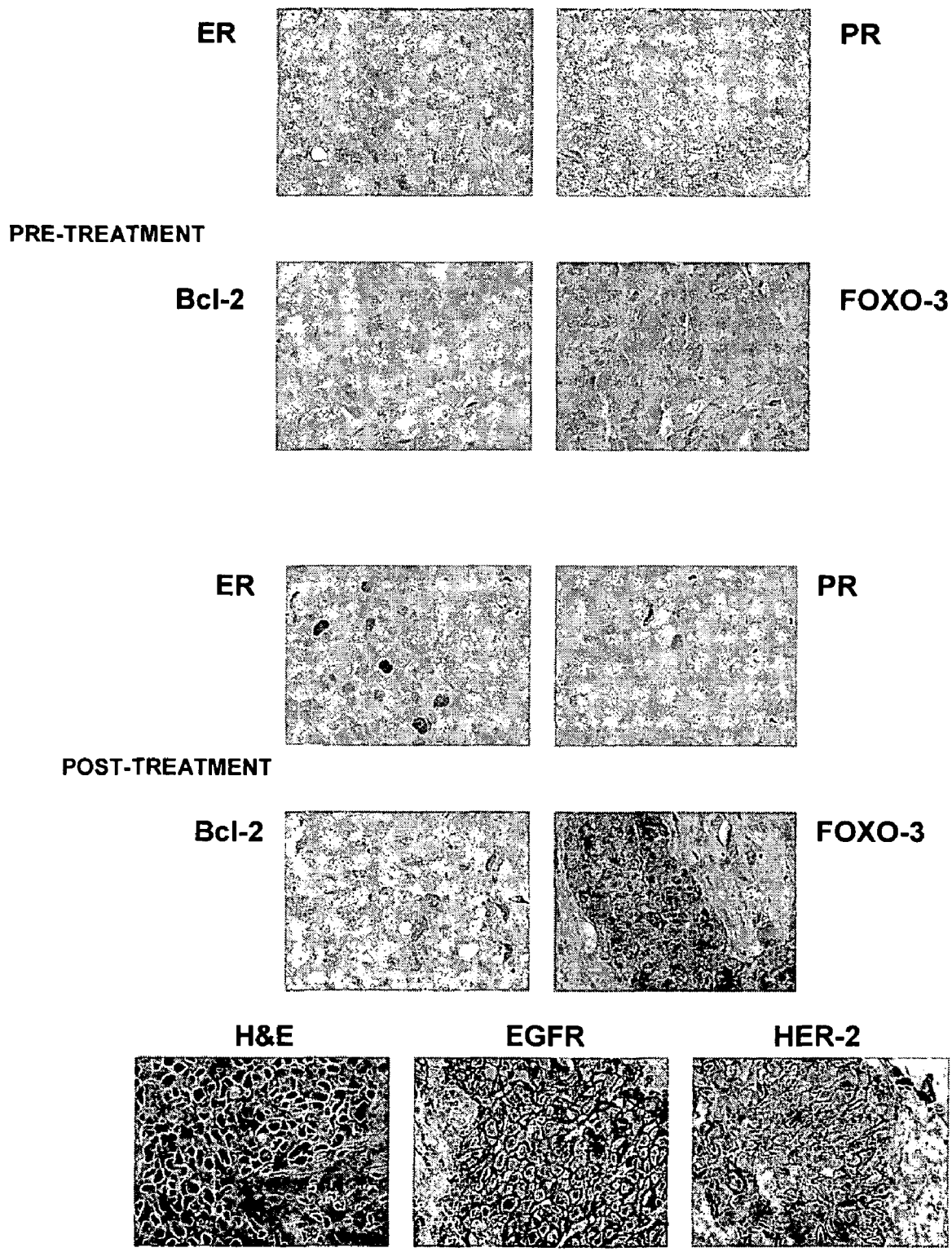
FIG. 18 is a series of photographs of breast cancer tissues stained using IHC and showing upregulation of ER following treatment with a dual EGFR/HER2 inhibitor.
Figure 19:
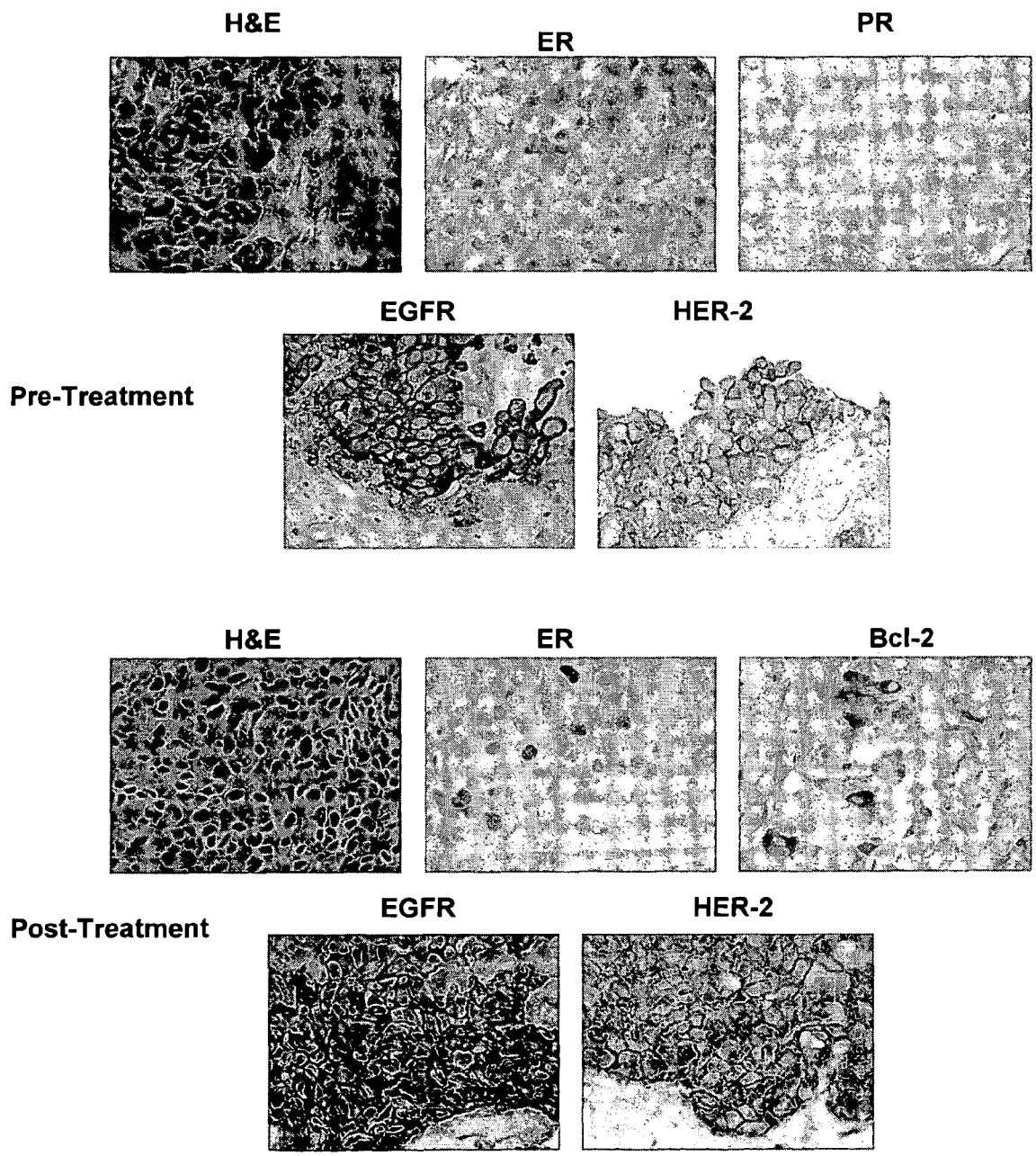
FIG. 19 is a series of photographs of breast cancer tissues stained using IHC and showing upregulation of ER following treatment with a dual EGFR/HER2 inhibitor.
Figure 20:
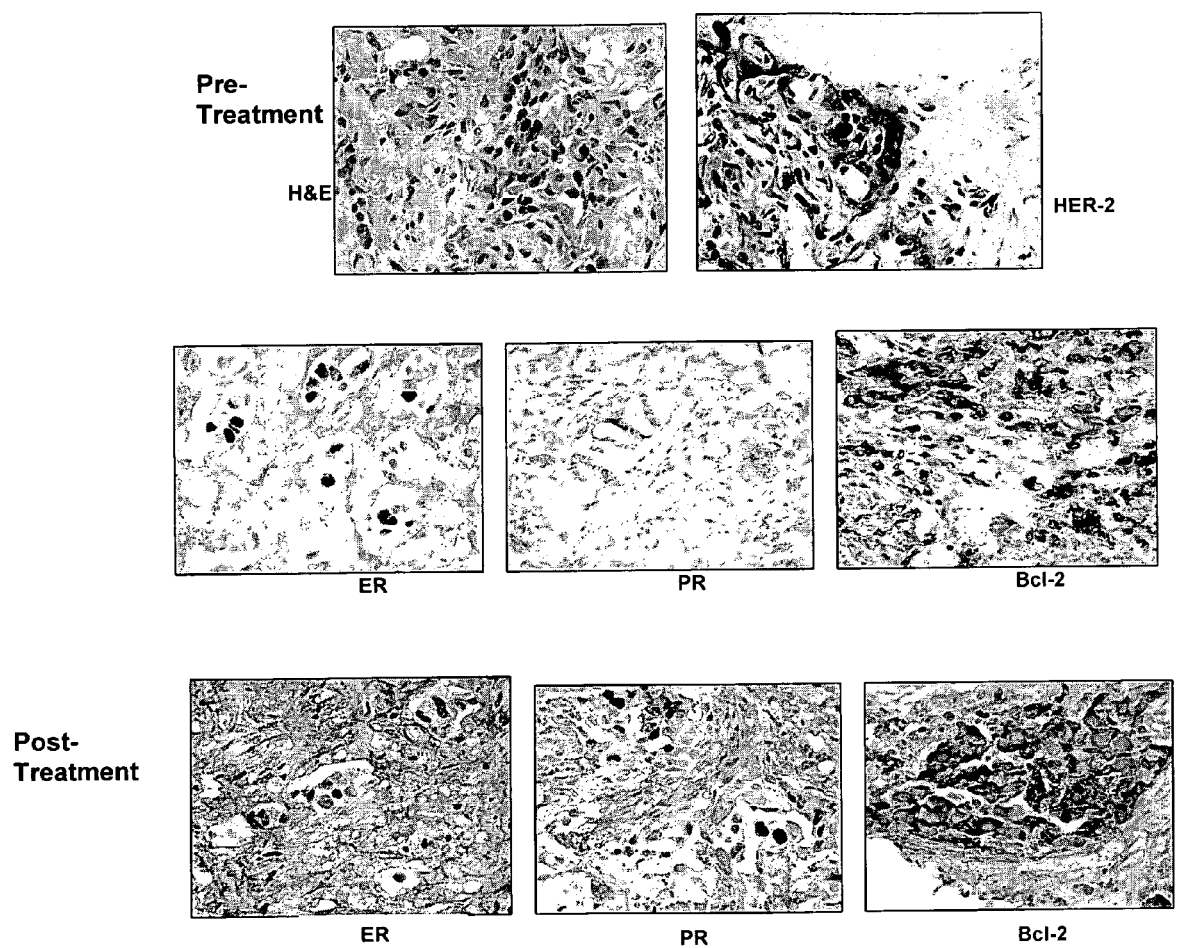
FIG. 20 is a series of photographs of breast cancer tissues stained using IHC and showing upregulation of ER following treatment with a dual EGFR/HER2 inhibitor.
Figure 24:
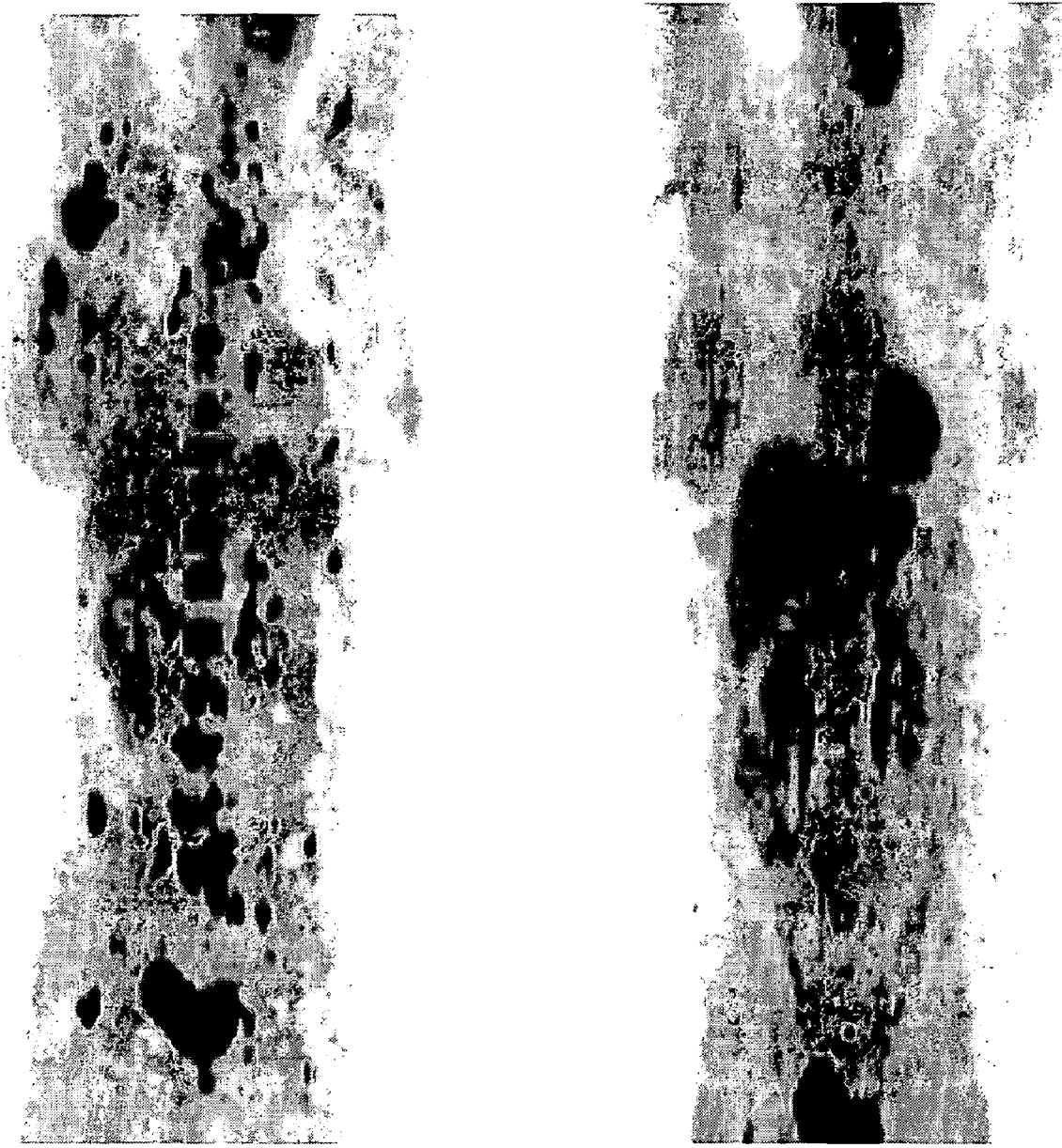
FIG. 24 is a series of photographs showing a patient's PET scar before and after treatment with an EGFR inhibitor together with an aromatase inhibitor.

One method for detecting PCD in a tissue sample is commonly referred to as the "TUNEL method." In this method, the 3' ends of the DNA fragments generated in apoptotic cells are labeled with biotin-coupled uridine (dUTP) using the enzyme terminal deoxynucleotidyl transferase (TdT). The biotin label is then detected with enzyme tagged streptavidin or avidin, which binds to biotin. When the colorless substrate of the enzyme is added to a tissue section or cell culture, it is reacted upon to produce a colored precipitate only in cells that have undergone apoptosis. See FIG. 15.

All TUNEL solutions and staining reagents used in the present invention were purchased from Roche. Paraffin-embedded tissue clinical samples were dewaxed and rehydrated by heating at 60° C. followed by washing in xylene and rehydration through a graded series of washes with ethanol and double distilled water. Samples were incubated for 15-30 min at 21-37° C. with Proteinase K. Slides were rinsed twice with PBS. The area around the sample was dried and 50 µl of TUNEL reaction mixture was added to each slide. A coverslip was added to each slide and incubated for 60 min at 37° C. in a humidified chamber in the dark. The slides were rinsed three times with PBS.

The TUNEL signal was converted by first drying the area around the sample and then adding 50 µl of Converter-POD reagent. The slides were incubated in a humidified chamber for 30 min at 37° C. and then rinsed three times in PBS. 100 µl of DAB Substrate was added to each slide and incubated for 10 min at 15-25° C. The slides were then rinsed three times with PBS. Slides were mounted under glass coverslips and TUNEL staining was analyzed under a light microscope.

For cryopreserved tissue, tissue sections were fixed with Fixation Solution for 20 min at 15-25° C., and then washed for 30 min in PBS. The sections were incubated with Blocking Solution for 10 min at 15-25° C. and rinsed with PBS. The sections were incubated in Permeabilisation Solution for 2 min on ice. Labeling and analysis were performed as described above for paraffin sections.

FIG. 14 shows significantly increased levels of PCD, as detected by TUNEL staining (using the above described methods) at 21 days after treatment with GW572016 in a patient with invasive breast carcinoma. See also Spector. 2005. 23(11): 2502-12.

Example 4

Outcome Determination Using TUNEL

Data on patient survival and efficacy of treatment indicated that patients with an intact PCD pathway were more responsive to therapeutic agent treatment than patients with a compromised PCD pathway.

PCD was determined by TUNEL staining of tumor biopsies or cell samples deposited on a slide. Patients that were positive for TUNEL staining had a better outcome than patients that were TUNEL negative, for both GW572016 and PKC412. For example, FIG. 14 shows a patient with invasive breast carcinoma (IBC) that was positive for TUNEL staining and responded well to GW572016 treatment. See also Spector et al., 2005. J. Clin. Oncology, 23(11): 2502-12.

Testing individuals for the presence of a functional PCD pathway prior to therapeutic agent treatment provides valuable information about whether a patient is likely to have a positive outcome. Testing for a functional PCD can be accomplished by several different protocols, including but not limited to TUNEL staining of tissue biopsies and determination of caspase activity on cultured cells from biopsies or from single cells derived from patient effusions. Caspase activation is a reliable indicator of a functional PCD pathway because caspases are the final mediators of PCD in the cell.

Example 5

Targeted Therapy Marker Profile of a Subject Achieving More than 20 Months of a Disease Free State Following Treatment with a Small Molecule Dual Inhibitor of EGFR/erbB2

Using standard procedures, tissue samples were obtained from a subject that has achieved more than 20 months of a disease free state following treatment with a small molecular dual inhibitor of EGFR/erbB2. In particular, tissue samples of 4-5 µm embedded in paraffin sections were dried at 60° C. for 1 h and then subsequently deparaffinized using sequential hydrating washes of decreasing alcohol concentrations to deionized water per standard procedures. Sections of the tissue samples, specific for ER and PR, were then heat antigen retrieved with citrate target retrieval solution (DakoCytomation, Carpinteria, Calif.), while sections of the tissue samples specific for Bcl-2 were heat antigen retrieved with DakoCytomation EDTA target retrieval solution, pH 9, in the Biocare decloaking chamber (Walnut Creek, Calif.) at the manufacturer's suggested default times. The slides were immediately removed from the decloaking chamber, washed well with deionized water and loaded onto the DakoCytomation automated IHC "Autostainer" staining platform. The sections were then immuno-stained with 3% hydrogen peroxide quench for 5 minutes. The primary antibodies (DakoCytomation) were diluted with Dako antibody dilution buffer as follows: ER and PR were diluted 1:200 and incubated for 15 minutes; and Bcl-2 was diluted 1:50 and incubated for 30 minutes. Next, the samples were incubated with DakoCytomation Envision+Dual Peroxidase Polymer. The ER and PR samples were incubated for 15 min while the Bcl-2 sample was incubated for 30 minutes. Finally, DakoCytomation DAB+ was applied to the sections, which were then incubated for 5 min. There were programmed TBS rinses between each incubation period and the slides were counterstained with DakoCytomation methyl green after being taken off the autostainer.

The results of this analysis, which illustrate a targeted therapy marker expression pattern or profile for a subject that achieved a complete response to lapatinib treatment for at least 20 months following treatment, are shown in FIG. 2.

Example 6

A Dual EGFR/erbB2 Small Molecule Inhibitor Causes More Cell Death in the Presence of Tamoxifen in BT474 Breast Tumor Cells Exponentially growing BT474 cells were treated with 1 μM estrogen for 24 hr. After 24 hr the cells were either untreated or treated with 5 μM small molecule dual inhibitor of EGFR/erbB2 (Sigma, GW2974) for 90 min. After 90 min, the cells were either untreated or treated with 10 μM tamoxifen for 72 hr. Cells were then washed with 1×PBS, stained with methylene blue (1% methylene blue in 50% methanol), rinsed with water, and dried overnight.

The results for this analysis are shown in FIG. 3. These results demonstrate that tamoxifen inhibition of ER activity increases the efficacy of cell killing by EGFR/erbB2 inhibitor treatments such as lapatinib or Sigma brand generic drug, GW2974. Thus, these results support that inhibition of ER activity increases the efficacy of EGFR/erbB2 inhibitors.

Example 7

Tissue Microarray Retrospective Analysis

Tissue samples were obtained from female subjects who showed overexpression of ErbB2 in the HerceptTest® (Genentech, Inc., San Francisco, Calif.) and analyzed using standard IHC techniques prior to treatment. In particular, the tissue samples were analyzed for expression of EGFR, ErbB3, p-erbB2, IGF-1R, NDF, and TGFα.

The female subjects supplying the tissue samples underwent HERCEPTIN® therapy plus chemotherapy. Table III below shows the percentage of subjects who responded to this therapy as well as those who did not. Patient outcome is correlated to expression of the above-identified targeted therapy markers in Table III. Statistical analysis was performed to quantify frequencies and calculate Pearson $x^2$ tests of significance for interactions between variables.

TABLE III

Receptor tyrosine kinase and ligand expression correlated with patient outcome

| Patient Group | N | % Responders | % Non-Responders | $X^2$ value/p-value |
|---|---|---|---|---|
| EGFR positive | 43 | 30 | 70 | 3.97/0.05 |
| EGFR negative | 23 | 9 | 91 | |
| Total: | 66 | 23 | 77 | |
| erbB3 positive | 70 | 29 | 71 | 0.62/NS |
| erbB3 negative | 7 | 43 | 57 | |
| Total: | 77 | 30 | 70 | |
| p-erbB2 positive | 17 | 23 | 77 | 0.42/NS |
| p-erbB2 negative | 60 | 32 | 68 | |
| Total: | 77 | 30 | 70 | |

TABLE III-continued

Receptor tyrosine kinase and ligand expression correlated with patient outcome

| Patient Group | N | % Responders | % Non-Responders | $X^2$ value/p-value |
|---|---|---|---|---|
| IGF-1R positive | 33 | 24 | 76 | 1.93/NS |
| IGF-1R negative | 35 | 40 | 60 | |
| Total: | 68 | 32 | 68 | |
| NDF positive | 55 | 39 | 62 | 6.35/NS |
| NDF negative | 22 | 9 | 91 | |
| Total: | 77 | 30 | 70 | |
| TGFα positive | 38 | 34 | 66 | 0.34/NS |
| TGFα negative | 29 | 28 | 72 | |
| Total: | 67 | 31 | 69 | |

As Table III demonstrates, while some targeted therapy markers by themselves are useful (EGFR.sup.- and NDF.sup.-patients are highly unlikely to respond to therapy with a dual EGFR/HER2 inhibitor such as HERCEPTIN® (Genentech, Inc., San Francisco, Calif.)), an analysis of a combination of targeted therapy markers provides a much higher likelihood of accurately predicting patient outcome, as shown below in Table IV. For example, certain combinations of targeted therapy markers achieved a statistically significant predict power of 100%.

TABLE IV

Analysis of Combinations of Targeted Therapy Markers

| Targeted Therapy Marker Profile | N | % Responder | % Non-Responder | $X^2$ value/p-value |
|---|---|---|---|---|
| NDF neg/p-S6 pos/IGF-1R neg | 2 | 50 | 50 | 19.4/0.01 |
| NDF neg/p-S6 neg/IGF-1R neg | 9 | 11 | 89 | |
| NDF neg/p-S6 neg/IGF-1R pos | 4 | 0 | 100 | |
| NDF neg/p-S6 pos/IGF-1R pos | 4 | 0 | 100 | |
| NDF pos/p-S6 pos/IGF-1R neg | 7 | 100 | 0 | |
| NDF pos/p-S6 neg/IGF-1R pos | 16 | 44 | 56 | |
| NDF pos/p-S6 neg/IGF-1R neg | 14 | 36 | 64 | |
| Total: | 56 | 37 | 63 | |
| NDF neg/p-Erk pos/EGFR neg | 3 | 0 | 100 | 12.75/NS |
| NDF neg/p-Erk neg/EGFR neg | 4 | 0 | 100 | |
| NDF neg/p-Erk pos/EGFR pos | 10 | 20 | 80 | |
| NDF neg/p-Erk pos/EGFR pos | 6 | 0 | 100 | |
| NDF pos/p-Erk pos/EGFR neg | 5 | 0 | 100 | |
| NDF pos/p-Erk neg/EGFR pos | 13 | 54 | 46 | |
| NDF pos/p-Erk neg/EGFR neg | 6 | 17 | 83 | |
| NDF pos/p-Erk pos/EGFR pos | 18 | 28 | 72 | |
| Total: | 65 | 23 | 77 | |

Example 8

Overexpression of Bcl-2 Targeted Therapy Marker

High expression of ERα, PR, Bcl-2, plays a role in resistance to ErbB inhibitors. ERα and PR expression in breast cancer are negatively associated with response to dual EFGR/HER2 inhibitor. Bcl-2 is a transcriptional target of ERα and in vitro data showed that high levels of Bcl-2 could be refractory to treatment with a dual EGFR/HER2 inhibitor as shown in FIG. 6.

Au-565 breast cancer cells were obtained from the American Tissue Culture Collection, (deposit # CRL-2351) (Manassas, Va.) and were transfected with a Bcl-2 cDNA to express high levels of Bcl-2. Methods of transfecting cells are well known in the art and any known methods may be used in this example. Transfected Au-565 cells were then exposed to GW2974 (Sigma-Aldrich, St. Louis, Mo.), a dual EGFR/HER2 tyrosine kinase inhibitor. The transfected Au-565 cells expressing high levels of Bcl-2 were resistant to GW2974 treatment as shown in FIG. 6.

Example 9

Microarray for Analyzing a Panel of Targeted Therapy Markers

A microarray is prepared using a film-based microarray substrate such as the BioFilmChip™ available from AutoGenomics (Carlsbad, Calif.). The microarray can include the entire microarray system provided by AutoGenomics (Carlsbad, Calif.), which includes an Infiniti® Analyzer as a platform, Intellipac™ reagent management modules, and Qmatic™ operating software.

Oligonucleotides having favorable hybridization properties for use in the microarray are prepared for ten genes of interest that qualify as targeted therapy markers. In particular, oligonucleotides are prepared for ErbB1, ErbB2, ErbB3, ErbB4, IGF-1R, heregulin, TGF-α, ERα, PR, Bcl-2, and β-actin. β-actin will be used as a housekeeping control gene.

The microarray will be based on annealing of an oligonucleotide to its complementary cDNA target in a complex cDNA probe and primer extension of the oligonucleotide to produce a fluorescently labeled cDNA. Because hybridization of the oligonucleotide and extension of the cDNA occurs in a PCR reaction, each oligonucleotide contains a unique sequence that serves as a molecular zip code that attached to its complement on the microarray after the PCR reaction is complete. Detection occurs through visualization of the fluorescent signal on the microarray.

Total RNA from various tumor cell lines having different levels of expression (e.g. AU-565, BT-474, MCF-7, MDA-MB-453, HL-60) of the selected targeted therapy markers will be isolated and used to prepare cDNA probes. HL-60 does not express detectable levels of ErbB1, ErbB2, ErbB3, or ErbB4 and therefore cDNA probes created using this cell line may serve as the low expression control. The cDNA probes created from the other cell lines may serve as high expression controls.

Tamoxifen treatment of breast cancer cells stimulates the transcriptional activity of ERα, which leads to upregulation of PR and Bcl-2. Therefore, any of the above identified breast cancer cell lines may be treated with tamoxifen and following treatment total RNA may be isolated and used to prepare a cDNA probe. This probe should serve as the high expression control for PR and Bcl-2. Probes obtained from untreated breast cancer cell lines may be used as the low expression control.

Fluorescent signal detection will be performed using an onboard confocal microscope.

Detection parameters for the microarray will be designed to correlate to protein expression levels observed in clinical specimens. In particular, clinical samples will be obtained from a variety of tumor tissue samples obtained from patients with various clinical outcomes following treatment with particular courses of therapy. Immunohistochemistry (IHC) will be performed with all samples to determine protein expression levels for each targeted therapy marker used in the microarray referenced above (e.g. ErbB1, ErbB2, ErbB3, ErbB4, IGF-1R, heregulin, TGF-α, ERα, PR, Bcl-2, and β-actin). In addition to traditional pathology scores generated by IHC analysis, an image-based analysis will be performed on all IHC slides generated from the samples and a quantitative optical density (O.D.) value will be assigned to each IHC stained slide. Additionally, normal tissue samples will be analyzed and IHC and O.D. data will be collected for normal tissue, which can then be used to establish a baseline for each biomarker.

Example 10

Clinical Study

Patients providing informed consent are enrolled in an open labeled, randomized trial if their tumors (i) overexpress ErbB1 and/or ErbB2 (2+−3+IHC staining in >10% of tumor cells measured according to Herceptest standards), or (ii) demonstrate ErbB2 gene amplification by FISH, or (iii) express activate, phospho-ErbB1 or phospho-ErbB2 by IHC (2-3+ staining in >10% of tumor cells), and (iv) if they satisfy other eligibility criteria (e.g., adequate end-organ function).

Patients are randomized to one of five dose cohorts of a dual EGFR/HER2 inhibitor (500, 650, 900, 1200, or 1600 mg) administered p.o. daily on a continuous basis until evidence of disease progression or intolerable side effects. Tumor biopsies are obtained within 3 days of initiating dual EGFR/HER2 inhibitor treatment (d0) and again on d21, within 4-12 h after administration of a dual EGFR/HER2 inhibitor. Patients are monitored by physical exams, clinical chemistry and hematology blood tests, and formally re-staged after 8 weeks of treatment. RECIST criteria are used to assess clinical response in appropriate target lesions (Therasse, et al., J Natl Cancer Inst, 92: 205-216 (2000)).

Reagents and Cell Culture

The ErbB2 overexpressing human breast adenocarcinoma line BT474 (American Type Culture Collection, Manassas, Va.) and the ErbB1 expressing LICR-LON-HN5 head and neck carcinoma cell line (HN5) are cultured as described in (Xia, et al., Oncogene (2002); Rusnak, et al., Mol Cancer Therap (2001)). A dual EGFR/HER2 inhibitor, such as GW572016 (synthesized as described in PCT Int. Appl. WO9935146, Glaxo Wellcome, (1999)), is dissolved in DMSO for cell culture work.

Anti-ErbB1, ErbB2, and cyclin D antibodies may be purchased from Dakocytomation (Carpanteria, Calif.). Anti-phospho-Akt (Ser 437) and phospho-Erk1/2 antibodies may be purchased from Cell Signaling Technology Inc., (Beverly, Mass.). Anti-phospho-ErbB1 antibodies may be purchased from Chemicon (Temecula, Calif.) and anti-TGFα, IGFR-1, and phosphor-ErbB2 antibodies from NeoMarkers (Fremont, Calif.). Anti-Erk1/2 antibodies may be purchased from Santa Cruz Biotechnology (Santa Cruz, Calif.).

The following antibodies can be used for Western blot analysis: anti-phosphotyrosine and actin antibodies were purchased from Sigma-Aldrich Chemical (St. Louis, Mo.), anti-ErbB1 (Ab-12) and anti-ErbB2 (Ab-11) antibodies from NeoMarkers, antibodies to phospho-Akt (Ser 437), phospho-Erk1/2, and Erk1/2 from Santa Cruz Biotechnology, and anti-cyclin D1 and 2 from Upstate Biotech (Lake Placid, N.Y.).

Immunohistochemistry

Biopsies are fixed in 10% Neutral Buffered Formalin (NBF) and paraffin-embedded sections prepared. Hemotoxylin and eosin staining are used to confirm the presence of tumor. Quantitative IHC may be performed as described in (Bacus, et al., Analyt Quant Cytol Histol (1997)). ErbB1, ErbB2, and cyclin D1 immunostaining may be performed using VMSI automated "BenchMark" staining module (Bacus, et al., Analyt Quant Cytol Histol (1997)). The VMSI "I-View" detection kit can be used for all three of the VMSI pre-diluted primary antibodies. Erk1/2 (1:1200), and TGFα (1:20) are immunostained using the "BenchMark" with I-VIEW detection chemistry. Phospho-Erk1/2 (1:100) and phospho-Akt (1:75) are immunostained using a labeled streptavidin peroxidase technique. Phospho-Erk1/2 and phosphor-Akt slides are antigen retrieved as described in (Bacus, et al., Analyt Quant Cytol Histol, (1997)). Slides are placed onto the Autostainer (Dako, Carpinteria, Calif.) and the "LSAB2 kit" (Dako) is employed as the detection chemistry. Phospho-ErbB1 (1:500) and phospho-ErbB2 (1:40) are immunostained in a similar labeled streptavidin peroxidase technique. Phospho-ErbB1 slides are antigen retrieved with 1 mM EDTA and slides for phospho-ErbB2 with 0.1M citrate buffer, pH 6.0, in the "decloaker". After staining, ErbB1, ErbB2, Erk1/2, phospho-Akt, phospho-Erk1/2, phospho-ErbB1, phospho-ErbB2, cyclin D1, IGFR-1, and TGFα are counterstained manually with 4% ethyl green (Sigma-Aldrich).

TUNEL Staining

TUNEL assay (Roche Diagnostics, Indianapolis, Ind.) is performed according to the manufacturer's instructions. The phosphor-Erk index is the product of the percentage of cells staining positive for phosphor-Erk1/2 in the tissue section and the Optical Density (OD) value for phosphor-Erk1/2 immunoreactivity. Investigators preparing and analyzing tissue sections are blinded to both patient tumor type and response to treatment. ErbB2 OD values of <10, 10-15, >15 roughly correlate with 1, 2, 3+ in the HercepTest® standards, respectively.

All TUNEL solutions and staining reagents can be purchased from Roche. Paraffin-embedded tissue clinical samples are dewaxed and rehydrated by heating at 60° C. followed by washing in xylene and rehydration through a graded series of washes with ethanol and double distilled water. Samples are incubated for 15-30 min at 21-37° C. with Proteinase K. Slides are rinsed twice with PBS. The area around the sample is dried and 50 µl of TUNEL reaction mixture was added to each slide. A coverslip is added to each slide and incubated for 60 min at 37° C. in a humidified chamber in the dark. The slides are rinsed three times with PBS.

The TUNEL signal is converted by first drying the area around the sample and then adding 50 µl of Converter-POD reagent. The slides are incubated in a humidified chamber for 30 min at 37° C. and then rinsed three times in PBS. 100 µl of DAB substrate are added to each slide and incubated for 10 min at 15-25° C. The slides are then rinsed three times with PBS. Slides are mounted under glass coverslips and TUNEL staining is analyzed under a light microscope.

For cryopreserved tissue, tissue sections can be fixed with Fixation Solution for 20 min at 15-25° C., and then washed for 30 min in PBS. The sections are then incubated with Blocking Solution for 10 min at 15-25° C. and rinsed with PBS. The sections are incubated in Permeabilisation Solution for 2 min on ice. Labeling and analysis are performed as described above for paraffin sections.

Disaggregation of Tissue

Tumor specimens are washed in PBS and finely minced with scissors. The sections are placed in a small Petri dish and covered in a solution containing 0.6 U/mL dispase (Invitrogen) and 100 U/mL type I collagenase (Invitrogen) for 1 h at 37° C. Cells are pelleted by centrifugation and the enzyme solution is decanted. Cells are incubated in medium with supplements and FBS and allowed to attach to the tissue culture plate at 37° C. in a $CO_2$ incubator.

Caspase Assay

Cells from tumor specimens are plated in 96-well white-walled tissue culture plates. The day after plating, cells are treated with therapeutic agent (GW572016, etc.) for 4-24 h. Following therapeutic agent treatment, plates are removed from the incubator and allowed to cool to room temperature. An equal volume of Caspase-Glo Reagent (either 3/7, 8, or 9, depending on the type of caspase assay—Promega) is added to the cell culture medium. Plates are gently rocked to mix the reagent and incubated for 30 min to 3 h, depending on cell type. Luminescence is measured using a Dynatech ML1000 Luminescence Plate Reader.

REFERENCES

U.S. Pat. No. 5,837,832
U.S. Pat. No. 5,807,522
WO 99 35146
WO 02 02552
WO 95 11995
Bacus S S, Chin D, Stewart J, Zelnick C, Mahvi D, Gilchrist K. Potential use of image analysis for the evaluation of cellular predicting factors for therapeutic response in breast cancers. *Anal Quant Cytol Histol*. 1997. Aug. 19(4): 316-28.
Bacus S S, Zelnick C R, Plowman G, Yarden Y. Expression of the erbB-2 family of growth factor receptors and their ligands in breast cancers. Implication for tumor biology and clinical behavior. *Am J Clin Pathol*. 1994. 102(4 Suppl 1):S13-24.
Balana M E, Lupu R, Labriola L, Charreau E H, Elizalde P V. Interactions between progestins and heregulin (HRG) signaling pathways: HRG acts as mediator of progestins proliferative effects in mouse mammary adenocarcinomas. *Oncogene*. 1999. 18:6370-79.
Baldwin, A S. Control of oncogenes and cancer therapy resistance by the transcription factor NF-kB. *J. Clin. Invest*. 2001. 107:241-246.
Bue P, Wester K, Sjostrom A, Holmberg A, Nilsson S, Carlsson J, Westlin J E, Busch C, Malmstrom P U. Expression of epidermal growth factor receptor in urinary bladder cancer metastases. *Int. J. Cancer*. 1998. 76(2):189-193.
Chow N H, Chan S H, Tzai T S, Ho C L, Liu H S. Expression profiles of ErbB family receptors and prognosis in primary transitional cell carcinoma of the urinary bladder. *Clin Cancer Res*. 2001. 7:1957-62.
Clem, R J., Cheng, E H, and Karp, C L. Modulation of cell death by Bcl-XL through caspase interaction. *Proc Natl Acad Sci, USA*. 1998. 95:554-559.
Cobleigh M A, Vogel C L, Tripathy D, Robert N J, Scholl S, Fehrenbacher L, Wolter J M, Paton V, Shak S, Lieberman G, Slamon D J. Multinational study of the efficacy and safety of humanized anti-HER2 monoclonal antibody in women who have HER2-overexpressing metastatic breast cancer that has progressed after chemotherapy for metastatic disease. *J. Clin. Oncol*. 1999. 17(9):2639-48.
Cockerill S, Stubberfield C, Stables J, Carter M, Guntrip S, Smith K, McKeown S, Shaw R, Topley P, Thomsen L, Affleck K, Jowett A, Hayes D, Willson M, Woollard P, Spalding D. Indazolylamino quinazolines and pyridopyrimidines as inhibitors of the EGFr and C-erbB-2. *Bioorganic Med. Chem. Letts*. 2001. 11:1401-5.
Dabrowski A, Filip A, Zgodzinski W, Dabrowska M, Polanska D, Wojcik M, Zinkiewicz K, Wallner G. Assessment of prognostic significance of cytoplasmic survivin expression in advanced oesophageal cancer. *Folia Histochem. Cytobiol*. 2004. 42(3):169-172.

Damstrup L, Rygaard K, Spang-Thomsen M, Poulsen H S. Expression of the epidermal growth factor receptor in human small cell lung cancer cell lines. *Cancer Res.* 1992. 52(11):3089-93.

Datta, S R, Brunet, A and Greenberg, M E. Cellular survival: a play in three Akts. *Genes Dev.* 1999. 13:2905-27.

Deveraux, Q L and Reed, J C. IAP family proteins-suppressors of apoptosis. *Genes Dev.* 1999. 13:239-252.

Di Cristofano, A, and Pandolfi, P P. The multiple roles of PTEN in tumor suppression. *Cell.* 2000. 100:387-390.

Dong L, Wang W, Wang F, Stoner M, Reed J C, Harigai M, Samudio I, Kladde M P, Vyhlidal C, Safe S. Mechanisms of transcriptional activation of bcl-2 gene expression by 17beta-estradiol in breast cancer cells. *J. Biol. Chem.* 1999. 274(45):32099-32107.

El-Deiry, W S. Role of oncogenes in resistance and killing by cancer therapeutic agents. *Curr. Opin. Oncol.* 1997. 9:79-87.

Evan, G I and Vousden, K H. Proliferation, cell cycle and apoptosis in cancer. *Nature.* 2001. 411:342-348.

Fry D W, Bridges A J, Denny W A, Doherty A, Greis K D, Hicks J L, Hook K E, Keller P R, Leopold W R, Loo J A, McNamara D J, Nelson J M, Sherwood V, Smaill J B, Trumpp-Kallmeyer S, Dobrusin E M. Specific, irreversible inactivation of the epidermal growth factor receptor and erbB2, by a new class of tyrosine kinase inhibitor. *Proc Natl Acad Sci, USA.* 1998. 95(20):12022-7.

Gibson, L., Holmgreen, S P, and Huang, D C. Bcl-w, a novel member of the bcl-2 family, promotes cell survival. *Oncogene.* 1996. 13:665-675.

Graus-Porta D, Beerli R R, Daly J M, Hynes N E. ErbB-2, the preferred heterodimerization partner of all ErbB receptors, is a mediator of lateral signaling. *EMBO J.* 1997. 16(7): 1647-55.

Gross M E, Zorbas M A, Danels Y J, Garcia R, Gallick G E, Olive M, Brattain M G, Boman B M, Yeoman L C. Cellular growth response to epidermal growth factor in colon carcinoma cells with an amplified epidermal growth factor receptor derived from a familial adenomatous polyposis patient. *Cancer Res.* 1991. 51(5):1452-9.

Harbour, J W and Dean, D C. Rb function in cell-cycle regulation and apoptosis. *Nat. Cell Biol.* 2000. 2:E65-67.

Hubbard S R. Structural analysis of receptor tyrosine kinases. *Prog. Biophys. Mol. Biol.* 1999. 71:343-358.

Johnstone R W, Ruefli A A, Lowe S W. Apoptosis: a link between cancer genetics and chemotherapy. *Cell.* 2002. 108(2):153-64.

Kanada N and Watanabe S. 17β-Estradiol Inhibits Oxidative Stress-Induced Apoptosis in Keratinocytes by Promoting Bcl-2 Expression. *J. Investigative Dermatology.* 2003. 121 (6):100-09.

Khanna, K K and Jackson, P S. DNA double-strand breaks: signaling, repair and the cancer connection. *Nat. Genet.* 2001. 27:247-254.

Klinge C M. Estrogen receptor interaction with co-activators and co-repressors. 2000. 65(5):227-251.

Leung L K, Do L, Wang T T. Regulation of death promoter Bak expression by cell density and 17 beta-estradiol in MCF-7 cells. *Cancer Letters.* 1998. 124:47-52.

Li, P, Nijhawan, D, and Budihardjo, I. Cytochrome c and dATP-dependent formation of Apaf-1/caspase-9 complex initiates an apoptotic protease cascade. *Cell.* 1997. 91:479-489.

Liu J W, Chandra D, Rudd M D, Butler A P, Pallotta V, Brown D, Coffer P J, Tang D G. Induction of prosurvival molecules by apoptotic stimuli: involvement of FOXO3a and ROS. *Oncogene.* 2005. 24(12):2020-31

Lockhart D J, Dong H, Byrne M C, Follettie M T, Gallo M V, Chee M S, Mittmann M, Wang C, Kobayashi M, Horton H, Brown E L. Expression monitoring by hybridization to high-density oligonucleotide arrays. *Nat. Biotech.,* 1996. 14:1675-80.

Lu Y, Zi X, Zhao Y, Mascarenhas D, Pollack M. Insulin-like Growth Factor-I Receptor Signaling and Resistance to Trastuzumab (Herceptin). Reports—*J. of Nat'l Cancer Institute,* 2001. 93(24): 1852-57.

Makin, G. Targeting apoptosis in cancer chemotherapy. *Expert Opin Ther Targets.* 2002. 6:73-84.

Muller H, Kueng W. Schoumacher F. Herzer S Eppenberger U. Selective Regulation of Steroid Receptor Expression in MCF-7 Breast Cancer Cells by a Novel Member of the Heregulin Family. *Biochem. And Biophys. Res. Comm.* 1995. 217(3):1271-78.

Murphy L C, Niu Y. Snell L, Watson P. Phospho-Serine 118 Estrogen Receptor-α Expression Is Associated with Better Disease Outcome in Women Treated with Tamoxifen. *Clin. Cancer Res.* 2004. 10:5902-06.

Muschen, M, Warskulat, U, and Becman, M W. Defining CD95 as a tumor suppressor gene. *J. Mol. Med.* 2000. 78:312-325.

Otter, S, Conus, and Ravn, U. The binding properties and biological activities of Bcl-2 and Bax in cells exposed to apoptotic stimuli. *J Biol Chem.* 1998. 273:6110-6120.

Paik, S. et al., A Multigene Assay to Predict Recurrence of Tamoxifen-Treated, Node-Negative Breast Cancer. *NE J. Med.* 2004. 351(27):2817-2826.

Perillo B, Sasso A, Abbondanza C, Palumbo G. 17beta-estradiol inhibits apoptosis in MCF-7 cells, inducing bcl-2 expression via two estrogen-responsive elements present in the coding sequence. *Mol. and Cell. Biol.* 2000. 20(8): 2890-91.

Perissi V, Menini N, Cottone E, Capello D, Sacco M, Montaldo F, De Bortoli M. AP-2 transcription factors in the regulation of ERBB2 gene transcription by oestrogen. *Oncogene,* 2000. 19:280-88.

Pinkas-Kramarski R, Eilam R, Alroy I, Levkowitz G, Lonai P, Yarden Y. Differential expression of NDF/neuregulin receptors ErbB-3 and ErbB-4 and involvement in inhibition of neuronal differentiation. *Oncogene.* 1997. 4; 15(23):2803-15.

Ranson M, Mansoor W, Jayson G. ZD1839 (IRESSA): a selective EGFR-TK inhibitor. *Expert Rev Anticancer Ther.* 2002. 2(2): 161-8.

Roymans, D and Slegers, H. Phospatidylinositol 3-kinases in tumor progression. *Eur. J. Biochem.* 2001. 268:487-98.

Rusnak D W, Lackey K, Affleck K, Wood E R, Alligood K J, Rhodes N, Keith B R, Murray D M, Knight W B, Mullin R J, Gilmer T M. The effects of the novel, reversible epidermal growth factor receptor/ErbB-2 tyrosine kinase inhibitor, GW2016, on the growth of human normal and tumor-derived cell lines in vitro and in vivo. *Mol Cancer Ther.* 2001. 1(2):85-94.

Rusnak D W, Affleck K, Cockerill S G, Stubberfield C, Harris R, Page M, Smith K J, Guntrip S B, Carter M C, Shaw R J, Jowett A, Stables J, Topley P, Wood E R, Brignola P S, Kadwell S H, Reep B R, Mullin R J, Alligood K J, Keith B R, Crosby R M, Murray D M, Knight W B, Gilmer T M, Lackey K. The characterization of novel, dual ErbB-2/ EGFR, tyrosine kinase inhibitors: potential therapy for cancer. *Cancer Res.* 2001. 61(19):7196-203.

Saceda M, Grunt T W, Colomer R, Lippman M E, Lupu R, Martin M B. Regulation of estrogen receptor concentration and activity by an erbB/HER ligand in breast carcinoma cell lines. *Endocrinology.* 1996. 137(10):4322-30.

Salomon D S, Brandt R, Ciardiello F, Normanno N. Epidermal growth factor-related peptides and their receptors in human malignancies. *Crit Rev Oncol Hematol.* 1995. 19(3):183-232.

Sargent E R, Gomella L G, Belldegrun A, Linehan W M, Kasid A. Epidermal growth factor receptor gene expression in normal human kidney and renal cell carcinoma. *J Urol.* 1989. 142(5):1364-8.

Schena M, Shalon D, Heller R, Chai A, Brown P O, Davis R W. Parallel human genome analysis: microarray-based expression monitoring of 1000 genes. *Proc. Natl. Acad. Sci.* 1996. 93(20):10614-9.

Sedlak, T W, Oltvai, Z N, and Yang, E. Multiple Bcl-2 family members demonstrate selective dimerizations with Bax. *Proc Natl Acad Sci, USA.* 1995. 92:7834-7838).

Sherr C J and Weber J D. The ARF/p53 pathway. *Curr. Opin. Genet. Dev.* 2000. 10:94-99.

Shin, M S, Kim, H S, Less, S H, Park, W S, Kim, S Y, Park, J Y, Lee, J H, Lee, S K, Lee, S N, Jung, S S. Mutations of tumor necrosis factor-related apoptosis-inducing ligand receptor 1 (TRAIL-R1) and receptor 2 (TRAIL-2) genes in metastatic breast cancers. *Cancer Res.* 2001. 61:4942-4946.

Sibilia M, Wagner E F. Strain-dependent epithelial defects in mice lacking the EGF receptor. *Science.* 1995. 269(5221): 234-8 (Erratum in: *Science.* 1995. 269(5226):909).

Slamon D J, Godolphin W, Jones L A, Holt J A, Wong S G, Keith D E, Levin W J, Stuart S G, Udove J, Ullrich A, et al. Studies of the HER-2/neu proto-oncogene in human breast and ovarian cancer. *Science.* 1989. 244(4905):707-12.

Smith B L, Chin D, Maltzman W, Crosby K, Hortobagyi G N, Bacus S S. The efficacy of Herceptin therapies is influenced by the expression of other erbB receptors, their ligands and the activation of downstream signaling proteins. *Br J Cancer.* 2004. 91(6):1190-4.

Soengas, M S, Capodieci, P, Polsky, D, Mora, J, Esteller, M, Opitz-Araya, X, McCombie, R, Herman, J G, Gerald, W L, Lazebinik, Y A. Inactivation of the apoptosis effector Apaf-1 in malignant melanoma. *Nature.* 2001. 409:207-211.

Spector N, et al., Correlation of Biological and Clinical Activity of Lapatinib. 2004. (uppublished results presented at ASCO, New Orleans) (available from inventor).

Spector N., et al., Study of the biologic effects of lapatinib, a reversible inhibitor of ErbB1 and ErbB2 tyrosine kinases, on tumor growth and survival pathways in patients with advanced malignancies. *J. Clin. Oncology.* 2005. 23(11): 2502-12.

Span P N, Sweep F C, Wiegerinck E T, Tjan-Heijnen V C, Manders P, Beex L V, de Kok J B. Survivin is an independent prognostic marker for risk stratification of breast cancer patients. *Clin. Chem.* 2004. 50(11):1986-93.

Teitz, T, Wei, T, Valentine, M C, Vanin, E F, Grenet, J, Valentine, C A, Behm, F G, Look, A T, Lahti, J M, Kidd, V J. Caspase-8 is deleted or silenced preferentially in childhood neuroblastomas with amplification of MYCN. *Nat. Med.* 2000. 6:529-535.

Tenzer A, Zingg D, Rocha S, Hemmings B, Fabbro D, Glanzmann C, Schubiger P A, Bodis S, Pruschy M. The phosphatidylinositide 3'-kinase/Akt survival pathway is a target for the anticancer and radiosensitizing agent PKC412, an inhibitor of protein kinase C. *Cancer Res.* 2001. 61 (22): 8203-10.

Tepper, C G and Seldin, M F. Modulation of casspase-8 and FLICE-inhibitory protein expression as a potential mechanism of Epstein-Barr virus tumorigenesis in Burkitt's lymphoma. *Blood.* 1999. 94:1727-137.

*The Molecular Basis of Cancer*, Mendelsohn and Israel, eds., Chapter 1, entitled "Cell cycle regulation, oncogenes, and antineoplastic drugs" by Murakami et al., (WB Saunders; Philadelphia, 1995), especially p. 13.

Threadgill D W, Dlugosz A A, Hansen L A, Tennenbaum T, Lichti U, Yee D, LaMantia C, Mourton T, Herrup K, Harris R C, et al. Targeted disruption of mouse EGF receptor: effect of genetic background on mutant phenotype. *Science.* 1995. 269(5221):230-4.

Turkeri L N, Erton M L, Cevik I, Akdas A. Impact of the expression of epidermal growth factor, transforming growth factor alpha, and epidermal growth factor receptor on the prognosis of superficial bladder cancer. *Urology.* 1998. 51(4):645-9.

Tzahar E, Waterman H, Chen X, Levkowitz G, Karunagaran D, Lavi S, Ratzkin B J, Yarden Y. A hierarchical network of interreceptor interactions determines signal transduction by Neu differentiation factor/neuregulin and epidermal growth factor. *Mol Cell Biol.* 1996. 16(10):5276-87.

Verbeek B S, Adriaansen-Slot S S, Vroom T M, Beckers T, Rijksen G. Overexpression of EGFR and c-erbB2 causes enhanced cell migration in human breast cancer cells and NIH3T3 fibroblasts. *FEBS Lett.* 1998. 425(1):145-50.

Vogelstein, B, Lan, D, Levine, A J. Surfing the p53 network. *Nature.* 2000. 408:307-310.

Weisberg E, Boulton C, Kelly L M, Manley P, Fabbro D, Meyer T, Gilliland D G, Griffin J D. Inhibition of mutant FLT3 receptors in leukemia cells by the small molecule tyrosine kinase inhibitor PKC412. *Cancer Cell.* 2002. 1(5):433-43.

Xia W, Mullin R J, Keith B R, Liu L H, Ma H, Rusnak D W, Owens G, Alligood K J, Spector N L. Anti-tumor activity of GW572016: a dual tyrosine kinase inhibitor blocks EGF activation of EGFR/erbB2 and downstream Erk1/2 and AKT pathways. *Oncogene.* 2002 Sep. 12; 21(41):6255-63.

The invention claimed is:

1. A method of predicting whether a subject will respond to treatment with a dual tyrosine kinase inhibitor, the method comprising:
   (a.) analyzing a sample obtained from the subject to determine expression levels for a panel of targeted therapy markers, wherein the panel comprises neu differentiation factor (NDF), P70 S6 kinase protein (P-S6), and insulin-like growth factor-1 receptor (IGF-1R); and
   (b.) predicting that the subject will be responsive to treatment with the dual tyrosine kinase inhibitor where the sample is NDF positive, P-S6 positive and IGF-1R negative; or predicting that the subject will be non-responsive to treatment with the dual tyrosine kinase inhibitor where the sample is NDF negative, P-S6 negative and IGF-1R positive or NDF negative, P-S6 positive and IGF-1R positive.

2. The method of claim 1, wherein the dual tyrosine kinase inhibitor is trastuzumab or gefitinib.

3. The method of claim 1, wherein the sample is a biopsy sample.

4. The method of claim 1, wherein the sample is from breast cancer tissue.

5. The method of claim 1, wherein the expression levels are measured by a method selected from the group consisting of an enzyme-linked immunosorbent assay (ELISA), a radioimmunoassay (RIA), a Western blot, and an immunohistochemical assay (IHC).

6. The method of claim 1, wherein the expression levels are measured by a method selected from the group consisting of Northern blotting, RT-PCR, and biochip-based methods.

7. The method of claim 1, wherein the panel of targeted therapy markers form a microarray.

8. The method of claim 7, wherein the microarray is a film-based microarray.

9. The method of claim 1, wherein the subject has cancer.

10. A diagnostic kit for predicting the likelihood of successful treatment of cancer with a dual tyrosine kinase inhibitor, the kit comprising:

(a.) a panel of targeted therapy markers including neu differentiation factor (NDF), P70 S6 kinase protein (P-S6), and insulin-like growth factor-1 receptor (IGF-1R); and (b.) instructions.

11. The diagnostic kit of claim 10, wherein the panel of targeted therapy markers is present on a microarray.

* * * * *